(12) United States Patent
Prince et al.

(10) Patent No.: US 6,892,089 B1
(45) Date of Patent: *May 10, 2005

(54) CARDIAC MOTION TRACKING USING CINE HARMONIC PHASE (HARP) MAGNETIC RESONANCE IMAGING

(75) Inventors: Jerry L. Prince, Lutherville, MD (US); Nael F. Osman, Baltimore, MD (US)

(73) Assignee: Johns Hopkins University, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 09/959,311
(22) PCT Filed: Apr. 14, 2000
(86) PCT No.: PCT/US00/10232
§ 371 (c)(1), (2), (4) Date: Dec. 20, 2001
(87) PCT Pub. No.: WO00/64344
PCT Pub. Date: Nov. 2, 2000

Related U.S. Application Data
(60) Provisional application No. 60/130,595, filed on Apr. 22, 1999.

(51) Int. Cl.[7] ............................................. A61B 5/055
(52) U.S. Cl. ........................ 600/410; 128/922; 324/309
(58) Field of Search .............................. 600/410, 413; 324/307, 309; 128/920, 922

(56) References Cited

U.S. PATENT DOCUMENTS

| | | | |
|---|---|---|---|
| 4,486,708 A | 12/1984 | Macovski | .................... 324/309 |
| 5,363,044 A | 11/1994 | Xiang et al. | ................. 324/309 |
| 5,910,728 A | 6/1999 | Sodickson | .................. 324/309 |
| 6,081,119 A | 6/2000 | Carson et al. | .............. 324/307 |
| 6,453,187 B1 * | 9/2002 | Prince et al. | ................ 600/410 |

* cited by examiner

Primary Examiner—Ruth S. Smith
(74) Attorney, Agent, or Firm—McKenna Long & Aldridge LLP

(57) ABSTRACT

The present invention relates to a method of measuring motion of an object such as a heart by magnetic resonance imaging. A pulse sequence is applied to spatially modulate a region of interest of the object and at least one first spectral peak is acquired from the Fourier domain of the spatially modulated object. The inverse Fourier transform information of the acquired first spectral-peaks is computed and a computed first harmonic phase image is determined from each spectral peak. The process is repeated to create a second harmonic phase image from each second spectral peak and the strain is determined from the first and second harmonic phase images. In a preferred embodiment, the method is employed to determine strain within the myocardium and to determine change in position of a point at two different times which may result in an increased distance or reduced distance. The method may be employed to determine the path of motion of a point through a sequence of tag images depicting movement of the heart. The method may be employed to determine circumferential strain and radial strain.

27 Claims, 19 Drawing Sheets

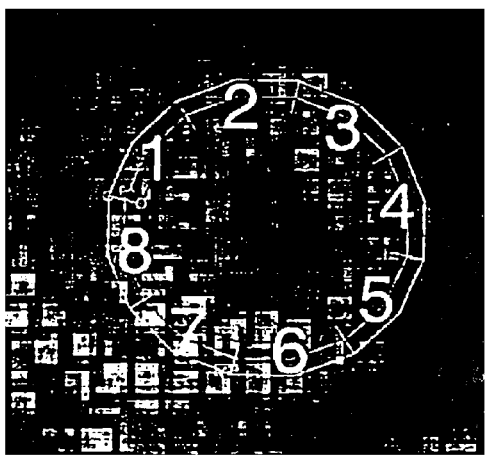 
FIG. 14a  FIG. 14b
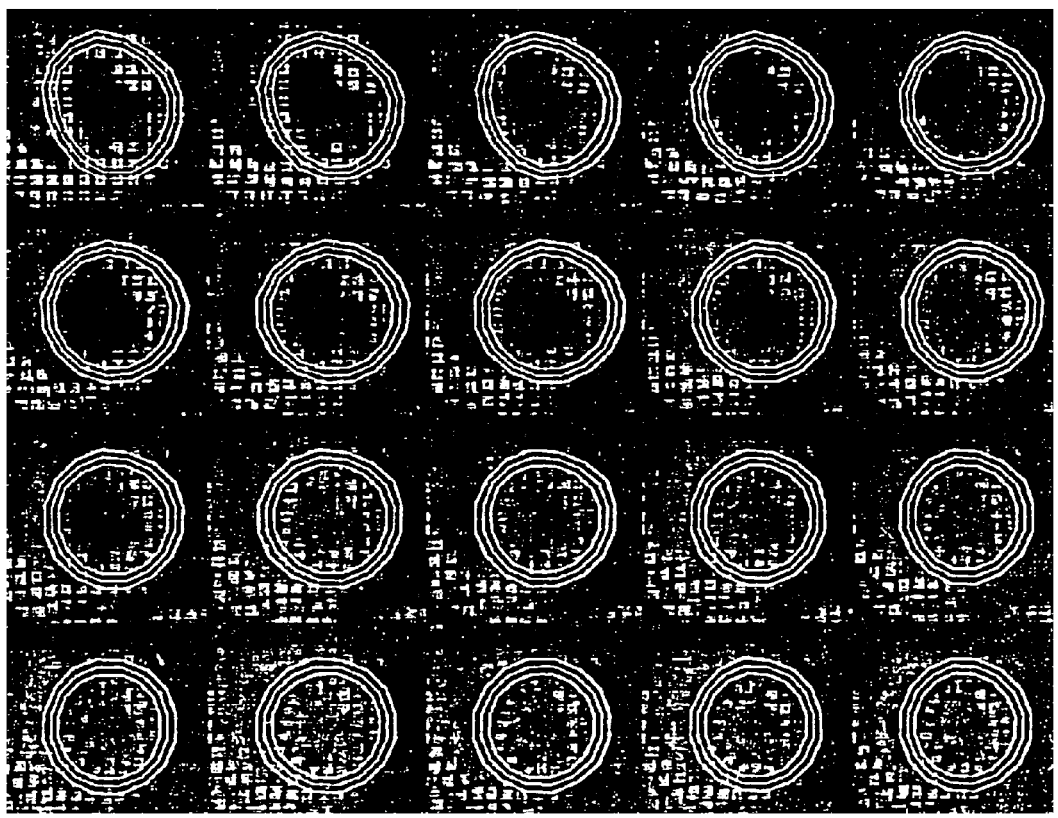
FIG. 14c

CARDIAC MOTION TRACKING USING CINE HARMONIC PHASE (HARP) MAGNETIC RESONANCE IMAGING

CROSS REFERENCE TO RELATED APPLICATION

This application claims the benefit of U.S. Provisional Application Serial No. 60/130,595, filed Apr. 22, 1999.

GOVERNMENT SUPPORT

The present invention was supported at least in part by NIH Grant No. R29 HL47405 and NSF Grant No. MIP93-50336.

BACKGROUND OF THE INVENTION

1. Field of the Invention

The present invention relates to the measurement of heart motion employing magnetic resonance imaging and, more specifically, it relates to a process of employing harmonic phase images acquired using magnetic resonance imaging in order to track material points and calculate Lagrangian strain in the heart.

2. Description of the Prior Art

The advantageous use of magnetic resonance imaging wherein a patient or object is placed within a magnetic field with alternating generation of RF pulses and gradient pulses serving to excite nuclei within the area of interest and cause responsive emission of magnetic energy which is picked up by a receiver and may be processed by computer means followed by recording, display or production of hard copy of the results has long been known. See, generally, Atalar-McVeigh U.S. Pat. No. 5,512,825 and Conturo-Robinson U.S. Pat. No. 5,281,914, both of which are assigned to the owner of the present invention, the disclosures of which are expressly incorporated herein by reference.

It has been known to employ two sets of tagging planes oriented orthogonal to the image plane in imaging two-dimensional heart wall motion with magnetic resonance imaging through spatial modulation of magnetization (SPAMM) approaches. See U.S. Pat. Nos. 5,054,489, 5,111,820 and 5,217,016. See also, Axel et al., "*MR Imaging of Motion with Spatial Modulation of Magnetization,*" Radiology, 171:841–845, 1989 and Axel et al., "*Heart Wall Motion: Improved Method of Spatial Modulation of Magnetization for MR Imaging,*" Radiology, 172(1):349–350, 1989.

It has been known in connection with magnetic resonance tagging to employ image processing techniques to detect tag features and subsequently combine the features into a detailed motion map related to displacement and strain with subsequent interpolation being employed. See, for example, Young et al., "*Three-Dimensional Motion and Deformation with Spatial Modulation of Magnetization,*" Radiology, 185:241–247, 1992 and McVeigh et al., "*Noninvasive Measurements of Transmural Gradients in Myocardial Strain with MR Imaging,*" Radiology, 180(3):677–683, 1991. These approaches are not automated, as they require some manual intervention.

It has also been known to employ optical flow methods in respect of magnetic resonance tagging image sequences. See, generally, Prince et al., "*Motion Estimation from Tagged MR Image Sequences,*" IEEE Trans. on Medical Imaging, 11(2):238–249, June 1992; Gupta et al., "*On Variable Brightness Optical Flow for Tagged MRI,*" Technical Report, 95-13, JHU/ECE, 1995; and Gupta et al., "*Bandpass Optical Flow for Tagged MR Imaging,*" Proceedings of the IEEE International Conf. on Image Proc., Santa Barbara, 1997. In such approaches sinusoidal tag patterns are employed instead of saturated planes. Image brightness gradients are features, which together with temporal derivatives estimated from image pairs, can be used to provide dense motion estimates generally referred to as "optical flow." Such approaches require regularization to compensate for the fact that the brightness gradients contain information about motion solely in the direction of the gradient.

U.S. Pat. No. 5,275,163 discloses the use of magnetic resonance imaging in monitoring motion of a part of an object. Pulse and gradient sequences are applied in pairs with spatially differing tagging patterns and subtraction being employed to form a tagged image.

U.S. Pat. No. 5,352,979 discloses observing a phase angle response of volume elements in a slice or volume and imaging occurring before and during perturbations caused by external stimuli.

U.S. Pat. No. 5,379,766 discloses quantitative motion evaluation of a portion of an object by employing a high contrast-tagging grid for detection of tagging patterns.

U.S. Pat. Nos. 5,315,248 and 5,545,993 disclose tracking of motion.

It has been known to employ planar tag analysis in magnetic resonance imaging. It has also been known to employ such approaches in connection with the analysis of myocardinal motion. Such prior art methods typically involve extraction of motion from these images through displacement vectors or strain patterns and involves tag identification and position estimation followed by interpolation.

Phase contrast magnetic resonance imaging has also been known. It provides a method for directly measuring motion by measuring a property sensitive to velocity and reconstructing velocity fields with strain being computed by employing finite differences. One of the problems with these two approaches is that planar tagging images cannot be accurately analyzed automatically. Phase contrast images, while capable of being analyzed automatically, tend to have a low signal-to-noise ratio leading to unacceptable results.

It has been known that strain measurements in the heart muscle can be significant in the diagnosis and quantification of heart disease. Developments over the past decade in tagged cardiac magnetic resonance imaging have made it possible to measure the detailed strain patterns of the myocardium in the in vivo heart. MR tagging employs a special pulse sequence to spatially modulate the longitudinal magnetization of the subject to create temporary features referred to as "tags" in the myocardium. Tagged MRI has been employed to develop and refine models of normal and abnormal myocardial motion, to better understand the correlation of coronary artery disease with myocardial motion abnormalities, to analyze cardiac activation patterns using pacemakers to understand the effects of treatment of myocardial infarction and in combination with stress testing for the early detection of myocardial eschemia. In spite of the successful scientific efforts, tagged MRI has been slow to enter into routine clinical use because of long imaging and post processing times, inadequate access to patients during imaging and lack of understanding of MR processing benefits by clinicians and their associates.

SUMMARY OF THE INVENTION

The term "angle image" as employed herein refers to the phase of an image corresponding to an isolated spectral peak in a SPAMM-tagged magnetic resonance image. This will also be referred to herein as a harmonic phase image or HARP image.

The present invention involves a method of measuring motion of an object by magnetic resonance imaging wherein a pulse sequence is applied to the spatially modulated region of interest of the object and at least one first spectral peak from the Fourier domain of the spatially modulated object is acquired. The inverse Fourier transform information of the acquired first spectral peaks is computed and a first harmonic phase image is computed from each of the spectral peaks. The process is repeated with respect to a different time to create a second harmonic phase image from each second spectral peak and strain is determined from the first and second harmonic phase images.

The method is particularly useful in tracking cardiac motion and in one approach involves determining both circumferential and radial Lagrangian strain. In a preferred embodiment, SPAMM pulse sequences are employed.

In one approach, the tracking of apparent motion through a CINE sequence of tag magnetic resonance images is employed.

It is an object of the present invention to provide an improved means of tracking cardiac motion employing magnetic resonance imaging.

It is a further object of the present invention to provide such a system which operates accurately and at a high rate of speed.

It is a further object of the present invention to provide a method which employs harmonic phase magnetic resonance imaging which tracks movement of a point and thereby by comparing sequences of images taken of a point taken at a different time facilitate determining strain within portions of the heart.

It is a further object of the present invention to provide such a system which permit imaging of both the anatomy of the heart and the tagged features that move with the heart employing harmonic phase image sequences which accurately track the movement of material points through time and thereby permit determination of Lagrangian strain.

It is an object of the present invention to provide an improved method for rapid and accurate visualization of motion of an object using tagged magnetic resonance images of an object.

It is another object of the present invention to provide such a method which employs isolated spectral peaks in SPAMM-tagged magnetic resonance images.

It is a further object of the present invention to provide such a system wherein angle images are acquired from two or more spectral peaks of the Fourier transform information and are employed to provide planar strain or tensor strain computations.

It is a further object of the present invention wherein angle images may be employed to make such computations automatically and rapidly.

It is yet another object of the present invention to produce angle images directly from the Fourier data without requiring production of conventional magnetic resonance images.

These and other objects of the invention will be more fully understood from the following description of the invention on reference to the illustrations appended hereto.

BRIEF DESCRIPTION OF THE DRAWINGS

FIG. 7b is the angle image of FIG. 7a.

FIG. 14(a) illustrates manually defined circles at end-systole.

FIG. 14(b) illustrates the deformed shape of the circles of FIG. 14(a) after tracking backward to end-diastole, and FIG. 14(c) illustrates the entire sequence of tracked circles.

DESCRIPTION OF THE PREFERRED EMBODIMENTS

Figure 1:
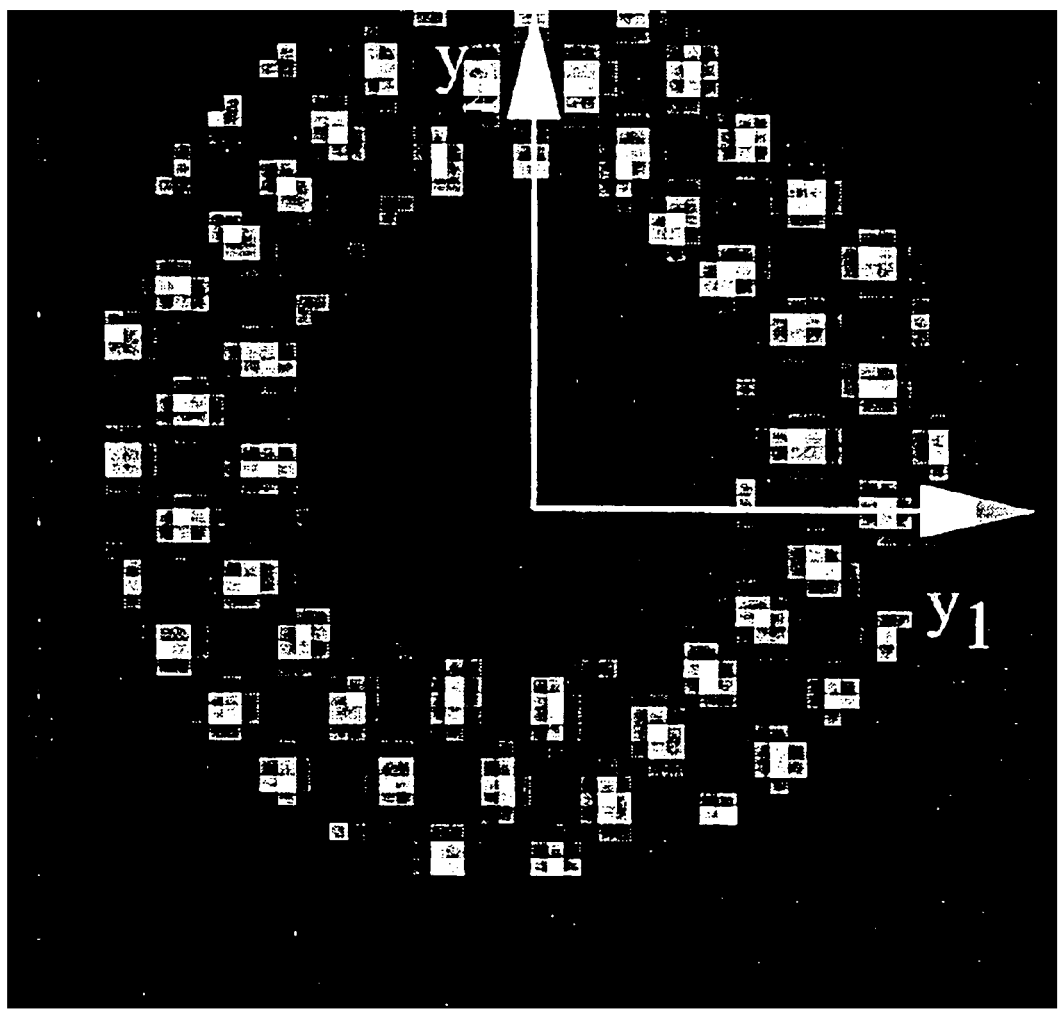
FIG. 1 illustrates a simulated two-dimensional 1—1 SPAMM tagged image.

As employed herein, the term "patient" means a living member of the animal kingdom including human beings.

As employed herein, the term "object" includes patients and any other items, as well as portions thereof, being monitored for movement by methods of the present invention. Among the medical uses are use in measuring motion of the heart wall, muscles and tendons. The object being monitored may be a fluid, such as blood or cerebrospinal fluid, for example, or a solid or semi-solid, or combinations thereof.

The following description of FIGS. 1–7(b) provides background information relevant to the invention disclosed and claimed in the present application and is the subject of the present inventors' U.S. patent application Ser. No. 09/131, 589. This prior application was physically a part of Provisional Application Serial No. 60/130,595 and is carried into the present application therefrom. The reference in the context of FIGS. 1–7(b) to "angle images" in the description of FIGS. 8–18 will be referred to as "harmonic phase images" or "HARP images."

Tagged magnetic resonance imaging (MRI) is rapidly becoming a standard approach to the detection and monitoring of heart motion defects caused by ischemia or infarction. See, Zerhouni et al., "*Human Heart: Tagging with MR Imaging—A Method for Noninvasive Assessment of Myocardial Motion,*" *Radiology,* Vol. 169, No. 1, pp. 59–63, 1988; McVeigh et al., "*Noninvasive Measurements of Transmural Gradients in Myocardial Strain With MR Imaging,*" *Radiology,* Vol. 180, No. 3, pp. 677–683, 1991; and Moore et al., "*Calculation of Three-Dimensional Left Ventricular Strains from Biplanar Tagged MR Images,*" *Journal of Mag. Res. Imaging,* Vol. 2, pp. 165–175, March/April 1992. Tagged MRI uses an MR scanner to temporarily change the magnetic properties of tissues in and around the heart in a pre-specified pattern, which can then be imaged as both the heart and the pattern undergo deformation. Analysis of the deformed patterns in the resulting image sequence yields information about the motion of the heart muscle within its walls. Image analysis is usually done using feature extraction methods, although optical flow methods have also been explored. See, also, Fischer et al., "*True Myocardial Motion Tracking,*" *Mag. Res. in Medicine,* Vol, 31, pp. 401–413, 1994; Denney et al., "*Reconstruction of 3-D Left Ventricular Motion from Planar Tagged Cardiac MR Images: An Estimation Theoretic Approach,*" *IEEE. Trans. Med. Imag.,* Vol. 14, No. 4, pp. 625–635, 1995; Prince et al., "*Motion Estimation from Tagged MR Image Sequences,*" *IEEE Trans. on Medical Imaging,* Vol. 11, pp. 238–249, June 1992; Amarture et al., "*A New Approach to Study Cardiac Motion: The Optical Flow of Cine MR Images,*" *Mag. Res. Med.,* Vol. 29, No. 1, pp. 59–67, 1993; and Gupta et al., "*Bandpass Optical Flow for Tagged MR Imaging,*" in the *Proceedings of the IEEE International Conf. on Image Proc.,* Vol. 3, pp, 364–367, (Santa Barbara), 1997.

A dense estimate of planar strain can be formed directly from SPAMM-tagged images without using conventional feature extraction or optical flow methods. See Osman et al., "*Direct Calculation of 2D Components of Myocardial Strain Using Sinusoidal MR Tagging,*" in *Proceedings of SPIE's International Symposium on Medical Imaging,* (San Diego, USA), 1998; Axel et al., "*MR Imaging of Motion with Spatial Modulation of Magnetization,*" *Radiology,* Vol. 171, pp. 841–845, 1989; and Axel et al., "*Heart Wall Motion; Improved Method of Spatial Modulation of Magnetization for MR Imaging,*" *Radiology,* Vol. 172, No. 1, pp. 349–350, 1989. This approach relies on a signal model for SPAMM patterns and the interpretation of motion as an angle modulation of the underlying carrier frequencies. The present invention creates angle images which can be useful directly in estimating very small displacements (such as error displacements), synthesizing tag lines and computing optical flow.

SPAMM-tagged magnetic resonance images have a collection of distinct spectral peaks in the Fourier domain. Each spectral peak contains information about the motion in a specific direction. The inverse Fourier transform of one of these peaks, extracted as by using a bandpass filter, is a complex image whose phase is linearly related to a directional component of the actual motion. This phase image is the "angle image" defined hereinbefore. It is constrained to lie in the $[-\pi, \pi)$ range (by the action of the standard inverse arctangent operator.) This is the angle-wrapping antifact. Even though an angle-wrapping artifact exists, the angle image can be employed to synthesize tag patterns, and pairs of angle images can be employed to measure small displacement fields, optical flow between image pairs without requiring regularization, as well as two-dimensional and three-dimensional strain.

The heart is repeatedly tagged at end-diastole using a two-dimensional or three-dimensional 1—1 SPAMM tag pattern. The tagging pulse sequences are imposed at the end-diastole which is the portion of the cardiac cycle wherein the left ventricle is full of blood and the heart is relatively slow-moving and the QRS complex of the ECG signals is present. For purposes of evaluation, the end-diastole can be considered a time when t=0 and the position of the points within the heart at end-diastole can be treated as a material coordinate system. During successive cardiac cycles, k-space is scanned using a standard steady-state gradient echo imaging pulse sequence to acquire the Fourier transform information encompassing at least one of the nine dominant spectral lobes in Fourier space. If more than one spectral peak is images, a bandpass filter is applied to extract only the information in one peak. The inverse Fourier transform of this data is taken without performing a conjugate symmetry operation. It is customary in MR imaging to perform a conjugate symmetry operation. The angle of the resulting complex image forms an angle image.

It will be appreciated that in lieu of employing scanning by gradient echo magnetic resonance imaging, alternate known means, such as spin echo, spiral magnetic, or echo planar magnetic resonance imaging may be employed, for example.

Figure 2:
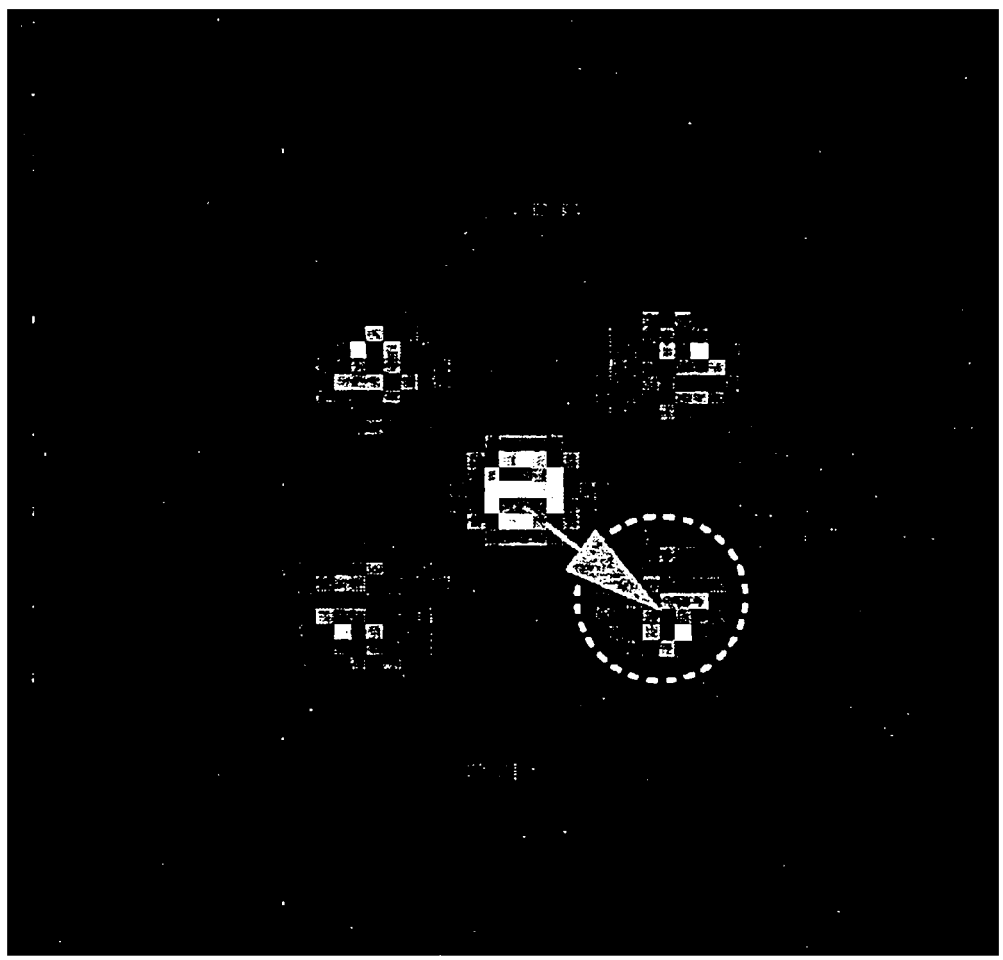
FIG. 2 illustrates the magnitude of the Fourier transform of the image of FIG. 1.

A one-dimensional 1—1 SPAMM tag pattern may be generated by applying a α-degree pulse followed by an applied transverse gradient pulse, which is within the image plane followed by another α-degree pulse with completion of the tag pattern being a crusher gradient, which eliminates coherent lateral magnetization. The 1D 1—1 SPAMM pattern is the sum of three complex images each occurring at different frequencies and resulting in the existence of three spectral peaks in the Fourier transform of the 1D 1—1 SPAMM-tagged image. A two-dimensional 1—1 SPAMM pattern may be created by applying two 1D 1—1 SPAMM sequences in rapid succession. This results in the 2D 1—1 SPAMM-tagged image being the sum of 9 complex images which result in 9 spectral peaks in such an image. A three-dimensional 1—1 SPAMM pattern may be created by applying three 1D 1—1 SPAMM pulse sequences in rapid succession. This results in the 3D 1—1 SPAMM tagged image being the sum of 27 complex images which results in 27 spectral peaks in the Fourier domain of such an image. In general, the number of the complex images and the spectral peaks in a tagged image depends on the number and properties of the SPAMM pulse sequence. A synthetic or simulated 2D 1—1 SPAMM pattern, which has been applied to a ring-shaped object is shown in FIG. 1 and the magnitude of its Fourier domain is shown in FIG. 2 showing the 9 spectral peaks.

The existence of these spectral peaks can be understood in the context of the tagging process providing a carrier harmonic, which spatially amplitude modulates the image, thereby causing a shift of its corresponding spectral peak to the position of the carrier harmonic.

To put this in mathematical context, a tagged MR image taken at time t can be represented by $\psi(y,t)$ which gives the intensity value at any point $y=[y_1 y_2]^T$ in the image plane, where $y_1$ is the read-out direction, and $y_2$ is the phase encoding direction. Because of the existence of spectral peaks the image $\psi(y,t)$ can be written as a summation $$\psi(y, t) = \sum_{k=-K}^{K} \psi_k(y, t) \tag{1}$$

wherein each image $\psi_k(y,t)$ is an image corresponding to a spectral peak. The integer k is an ID for a spectral peak. The location of the spectral peak is determined by the vector $w_k=[w_{1k} w_{2k} w_{3k}]^T$ which can be determined by the SPAMM pulse sequence. The total number of spectral peaks is 2K+1. Its value depends on the number and properties of the SPAMM pulse sequences.

The image $\psi_k$ is a complex image, i.e., has a magnitude ($D_k$) and phase ($\phi_k$) so that $$\psi_k(y,t)=D_k(y,t)e^{j\phi_k(y,t)}, k=-K, \ldots K \tag{2}$$

Under appropriate conditions, such as tags separation, $\psi_k$ can be extracted from $\psi$ using bandpass filters.

The angle images may be computed from the complex image $\psi_k$ using $$a_k(y,t) \equiv \angle \psi_k(y,t), k=-K, \ldots K \tag{3}$$

where $$\angle \psi_k = \begin{cases} \tan^{-1} \frac{\Im \psi_k}{\Re \psi_k} & \Re \psi_k \geq 0 \\ \pi + \tan^{-1} \frac{\Im \psi_k}{\Re \psi_k} & \text{otherwise} \end{cases} \tag{4}$$

wherein $\Im$ is an imaginary component part of the complex image and $\Re$ is the real part of the complex image.

Figure 3:
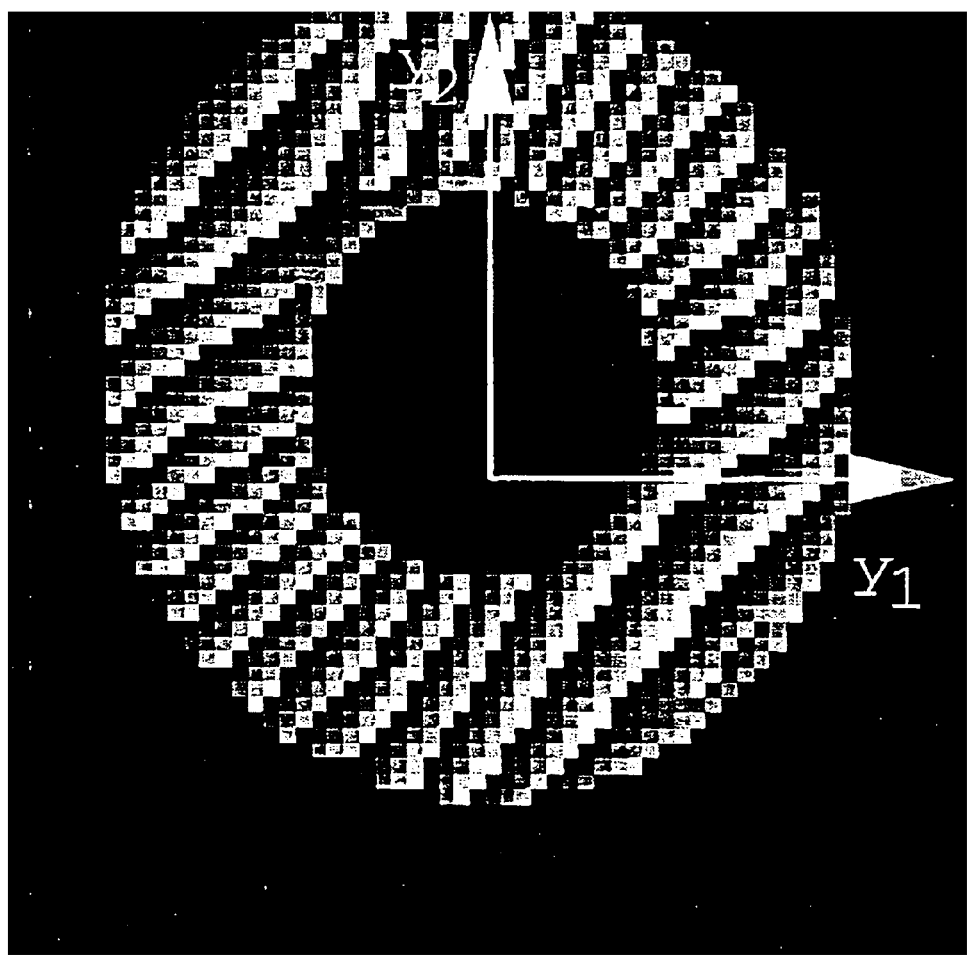
FIG. 3 illustrates the angle of the complex image.

For example, the angle image calculated from the spectral peak circled in FIG. 2 is shown in FIG. 3. The saw-tooth pattern of this image arise as a result of the angle of a complex quantity being wrapped into the range $[-\pi,\pi)$.

The angle images can be the basis for several very useful subsequent analyses. First, the images can be used to produce synthetic tags similar to the usual planar tags in tagged MRI images. The advantage of this feature is that the data is generated entirely automatically, and can be generated with any desired tag separation. Second, the images can be used directly to compute the small displacements of an object. Third, angle images can be used to directly compute planar strain in 2D-image plane, or a full 3D-strain tensor in 3D. These strain data are useful in the detection and quantification of myocardial ischemia and infarction. Fourth, the angle images can be used to form standard optical flow fields representing a time series of displacement fields.

Figure 4:
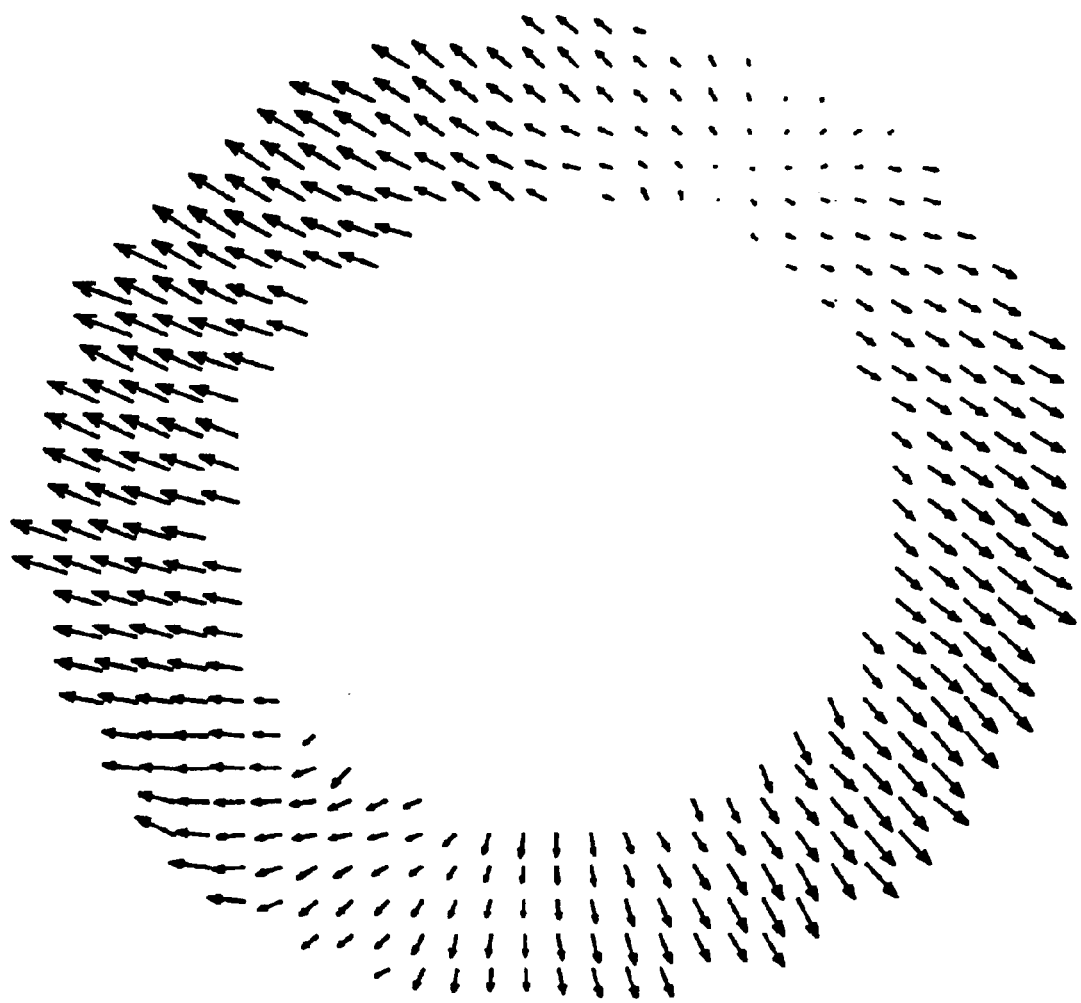
FIGS. 4 and 5 illustrate, respectively, (a) computed displacement of a point on the object and (b) with actual displacement.
Figure 5:
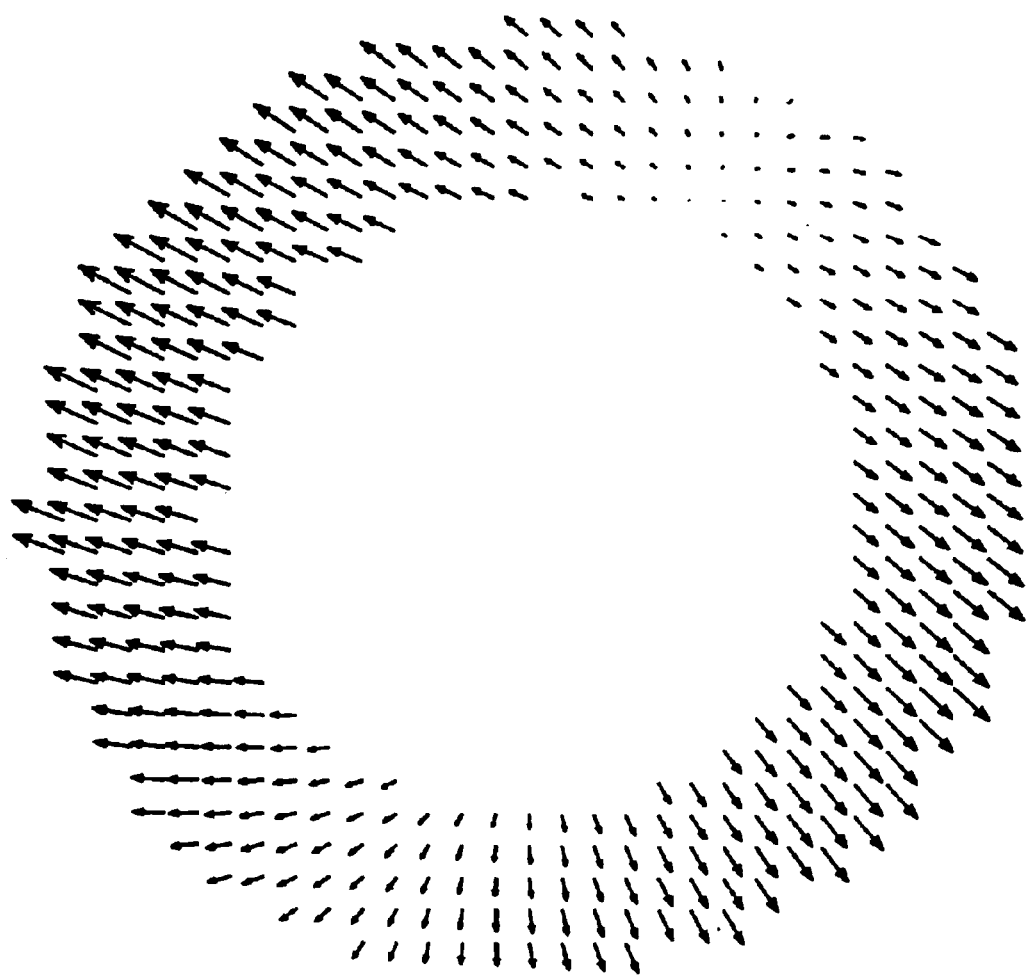

FIGS. 4 and 5 show the computed displacement and actual displacement, respectively, for a small displacement. The similarity between the computed and true displacement fields show that the motion of the angle images is effective to reconstruct the motion.

For synthetic tag lines of an image, a single angle image $a_k(y,t)$ can be employed. A tag line is a collection of points $\{y^*\}$ that satisfy $$a_k(y^*,t)=a \tag{5}$$

Figure 6:
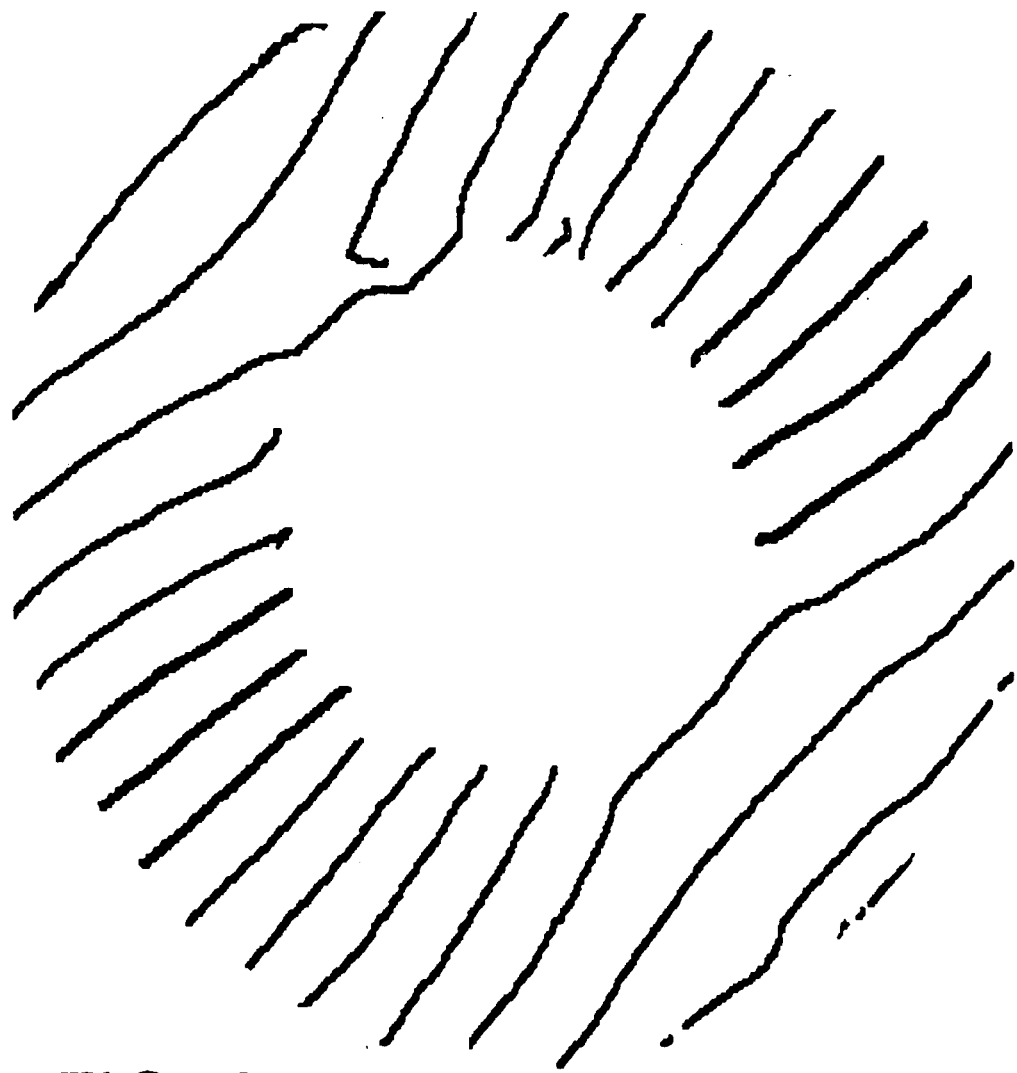
FIG. 6 illustrates computed displacement tag lines generated from the angle image shown in FIG. 3.

FIG. 6 shows tag lines generated from the angle image in FIG. 3. There are several advantages in using angle images to generate synthetic tag lines. First, it is a completely automatic process. Second, the tag lines will have subpixel resolution as good isocontour algorithms have this property. Third, the entire image will have these tags automatically identified, including, for example, both the left and right ventricular myocardium. Finally, by selecting N values in the range $[-\pi,\pi)$, N tag lines will be synthesized within over the spatial period $2\pi/w_k$. In principle, there is no fundamental limit on how closely these tag lines can be spaced, because they are not limited by the detectability of features spaced close together.

For small deformations, two angle images ($a_k$ and $a_l$) of two linearly independent vectors $w_k$ and $w_l$ that lie in the imaging plane can be used to compute the projection of the displacement field ($u_2$) on the image plane at t using $$u_2(y, t) = (W^T H)^{-1} \begin{bmatrix} \Delta a_k(y, t) \\ \Delta a_l(y, t) \end{bmatrix} \tag{6}$$

wherein W is the matrix and $^T$ is the transposition of the matrix and $\Delta a_k$ is computed by $$\Delta a_k(y,t)=W[w_k^T x(y)+\Theta_k a_k(y,t)] \tag{7}$$

$\Theta_k$ is a known angle determined from the pulse sequence and W is the nonlinear wrapping function given by $$W(\phi)=\text{mod}(\phi+\pi, 2\pi)=\pi \tag{8}$$

and the function x(y) maps any point y in the image plane coordinates system to its position $x \in \mathbb{R}^3$ in the magnets 3D coordinates system using $$x(y)=y_1 h_1+y_2 h_2+x_0=Hy+x_0 \tag{9}$$

where the matrix $H \in \mathbb{R}^{3\times 2}=[h_2 h_2]$, and the vectors $h_1 \in \mathbb{R}^3$ and $h_2 \in \mathbb{R}^3$ represent the readout and phase-encoding directions, respectively, of the image plane; and $x_0 \in \mathbb{R}^3$ is the image origin. The matrix $W \in \mathbb{R}^{3\times 2}=[w_1 w_2]$.

There are a number of ways to minimize the magnitude of motion being monitored to facilitate the method of the present invention being practiced on relatively small movements. One way, for example, is to image very shortly after end-diastole, before the heart has had a chance to move substantially. This approach will be useful and potentially clinically important in the first few tens of milliseconds of systole. Secondly, if low-frequency tag patterns are used, the physical period of the tag pattern is larger and larger motions will not produce angle ambiguity (wrapping). A potential difficulty with this option is that the spectral peaks of low-frequency patterns may interfere with another leading to undesired motion artifacts. A third approach would be to apply the tag pattern at a fixed offset from end-diastole and image shortly thereafter. In this case, the application of the tag pattern to rapidly moving tissue is required. Finally, a way to circumvent this problem is to image the displacement between image times rather than the displacement from the time of tagging. These displacements would be small. This approach is classically called "optical flow."

The strain is related to the difference in displacement between adjacent parts of tissue. This can be directly computed from at least two angle images ($a_k$ and $a_1$) of two linearly independent vectors $w_k$ and $w_1$. Planar strain in the direction e is computed by $$\epsilon_2(y, t; e) = \left\| (W^T H)^{-1} \begin{bmatrix} \nabla_y a_k^*(y, t) \\ \nabla_y a_l^*(y, t) \end{bmatrix} e \right\| - 1 \quad (10)$$

where $$\nabla_y a_k^* = \begin{cases} \nabla_y a_k & \|\nabla_y a_k\| \leq \|\nabla_y a_k^{(\pi)}\| \\ \nabla_y a_k^{(\pi)} & \text{otherwise} \end{cases} \quad (11)$$

and $$a_k^{(\pi)}(y,t) \equiv W(a(y,t)+\pi) \quad (12)$$

and similar equations for $\Delta_y a^*_1$. The last two equations are used to overcome the wrapping discontinuity while computing the derivatives of the angle images. The strain computed from these equations is in the Eulerian sense. A full strain tensor can be computed from three angle images coming from three spectral peaks. The generation of the three spectral peaks is done by using 3D SPAMM pattern and acquiring an image volume rather than an image plane.

Optional flow is defined as the apparent motion of brightness patterns in an image sequence. See, generally, E. C. Hildreth, "Measurement of Visual Motion," MIT Press, Cambridge, 1984. In the present context, the word "apparent" implies motion with the image plane instead of true 3D motion. In the prior art context, the definition of optical flow involves velocity fields, and generally some sort of regularization is required in order to get a dense estimate of this velocity field. See, generally, Horn et al., "Determining Optical Flow," Artificial Intelligence, 17:185–203, 1981. The usage of angle images within the context of the present invention, permits direct calculation of a velocity field without requiring the use of regularization.

For applying the angle images to optical flow methods, at least four angle images $a_k(y,t)$, $a_1(y,t)$, $a_k(y,t+\Delta t)$, and $a_1(y,t+\Delta t)$ with linearly independent vectors $w_k$ and $w_1$ may be employed. The time interval between two images $\Delta t > 0$ is preferably small enough for the assumption of constant motion velocity $v_2$ during the time interval. The planar motion velocity is computed by $$v_2(y, t) = \frac{-1}{\Delta t} \begin{bmatrix} \nabla_y a_k^*(y, t+\Delta t) \\ \nabla_y a_l^*(y, t+\Delta t) \end{bmatrix}^{-1} \begin{bmatrix} \nabla_t a_k(y) \\ \nabla_t a_l(y) \end{bmatrix} \quad (13)$$

where $$\Delta_t a_k(y) \equiv W[a_k(y,t+\Delta t) - a_k(y,t)] \quad (14)$$

Figure 7A:
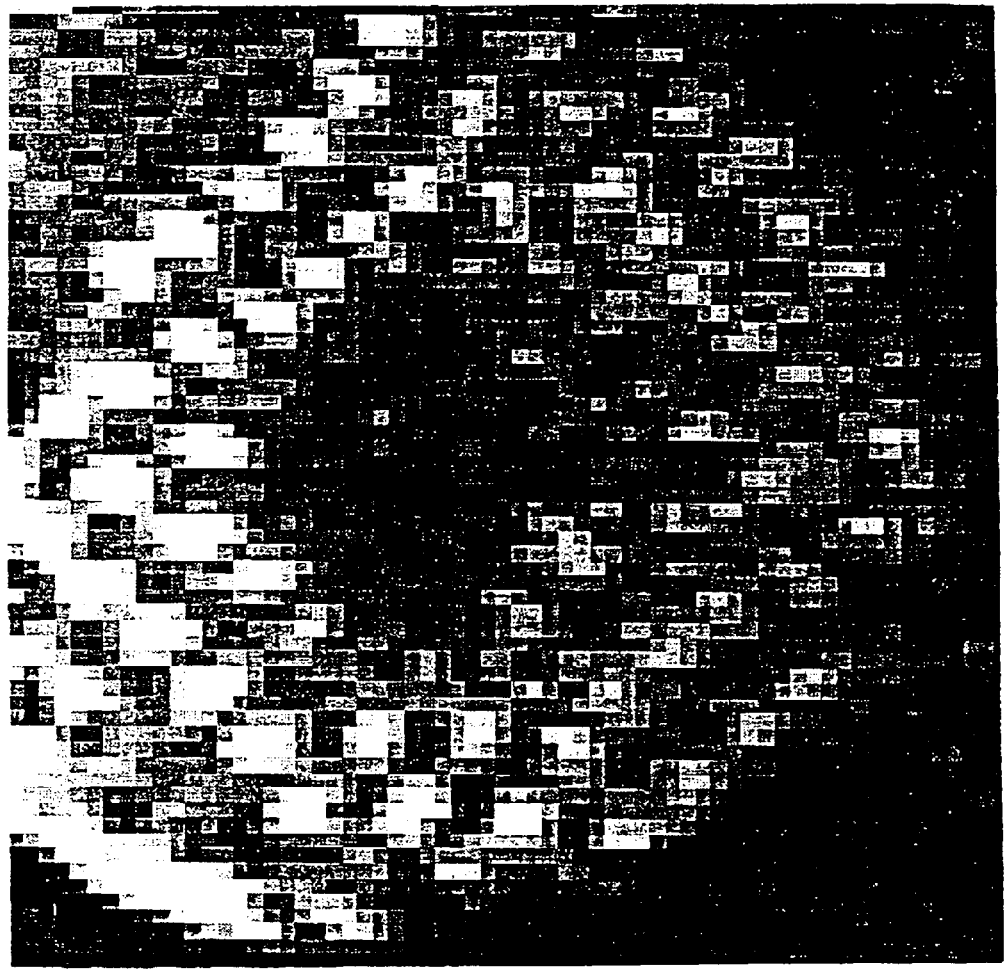
FIG. 7a is a cross-section of a left ventricle with 1—1 SPAMM tags.
Figure 7B:
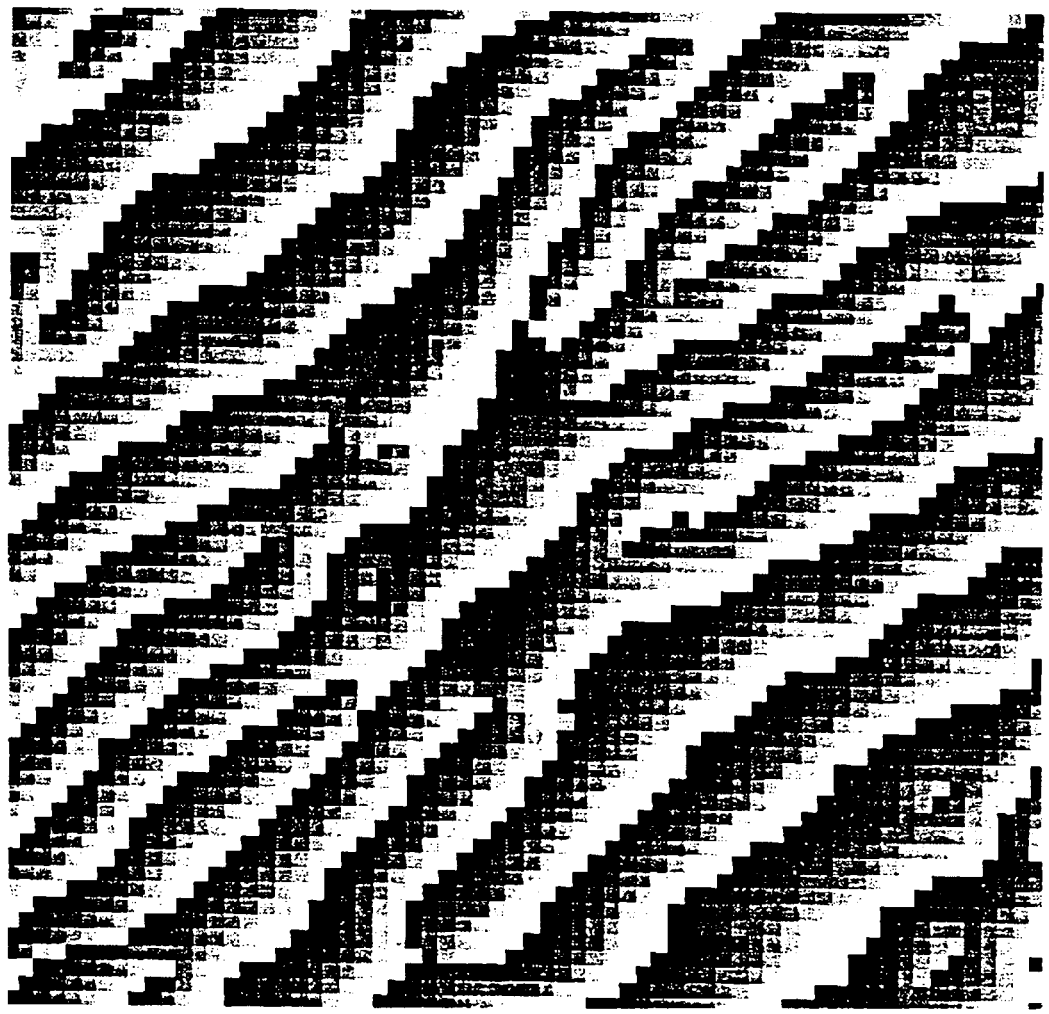

Referring to FIGS. 7a and 7b, FIG. 7a is a cross-section showing the left ventricle with 1—1 SPAMM tags. FIG. 7b shows the angle image created by the methods of the present invention of the left ventricular cross-section of FIG. 7a.

The present invention as exemplified in FIGS. 8 through 18 and the related disclosure provides image processing methods for rapid analysis of tagged cardiac magnetic resonance image sequences. The methods involve the use of isolated spectral peaks in SPAMM-tagged magnetic resonance images which contain information about the motion of the heart. The inverse Fourier transform of a SPAMM spectral peak is a complex image whose calculated angle is called a harmonic phase (HARP) image. The methods use two HARP image sequences to automatically and accurately track material points through time. In one embodiment, a rapid, semi-automated procedure uses these traces to calculate Lagrangian strain, including both circumferential and radial strain. These methods were developed within a two-dimensional context, but can be employed with three dimensions. This new computational approach permits rapid analysis and visualization within about 5–10 minutes after the scan is complete. Its performance may be demonstrated on MR image sequences reflecting both normal and abnormal cardiac motion.

Major developments over the past decade in tagged cardiac magnetic resonance imaging (Zerhouni et al., "Human heart: Tagging with MR imaging—a method for noninvasive assessment of myocardial motion," Radiology, 169(1):59–63, 1988; Axel et al., "MR imaging of motion with spatial modulation of magnetization," Radiology, 171:841–845, 1989; McVeigh et al., "Cardiac tagging with breath-hold cine MRI," Magn. Res. Med., 28:318–327, 1992; Fischer et al., "Improved myocardial tagging contrast," Magn. Res. Med., 30:191–200, 1993; Atalar et al., "Minimization of dead-periods in MRI pulse sequences for imaging oblique planes," Magn. Res. Med., 32(6):773–777, December 1994; and Fischer et al., "True myocardial motion tracking," Magn. Res. Med., 31:401–413, 1994) have made it possible to measure the detailed strain patterns of the myocardium in vivo heart. (Young et al., "Three-dimensional motion and deformation of the heart wall: Estimation with spatial modulation of magnetization—a model-based approach," Radiology, 185:241–247, 1992; Moore et al., "Calculation of three-dimensional left ventricular strains from biplanar tagged MR images," J. Magn. Res. Imag., 2(2):165–175, March/April 1992; Park et al., "Analysis of left ventricular wall motion based on volumetric deformable models and MRI-SPAMM," Med. Image Anal., 1(1):53–71, 1996; Denney, Jr. et al., "Model-free reconstruction of three-dimensional myocardial strain from planar tagged MR images," J. Magn. Res. Imag., 7:799–810, 1997; and E. R. McVeigh, "Regional myocardial function," Cardiology Clinics, 16(2):189–206, 1998). MR tagging uses a special pulse sequence to spatially modulate the longitudinal magnetization of the subject to create temporary features, called tags, in the myocardium. Fast spoiled gradient echo imaging techniques are used to create CINE sequences that show the motion of both the anatomy of the heart and the tag features that move with the heart. Analysis of the motion of the tag features in may images taken from different orientations and at different times can be used to track material points in 3-D, leading to detailed maps of the strain patterns within the myocardium. See, generally, E. R. McVeigh, "Regional myocardial function," Cardiology Clinics, 16(2):189–206, 1998 and E. R. McVeigh, "MRI of myocardial function: motion tracking techniques," Mag. Res. Imag., 14(2):137, 1996.

Tagged MRI has figured prominently in many recent medical research and scientific investigations. It has been used to develop and refine models of normal and abnormal myocardial motion (Moore et al., "Calculation of three-dimensional left ventricular strains from biplanar tagged MR images," J. Magn. Res. Imag., 2(2):165–175, March/April 1992; E. R. McVeigh, "MRI of myocardial function: motion tracking techniques," Mag. Res. Imag., 14(2):137, 1996; Clark et al., "Circumferential myocardial shortening in the normal human left ventricle," Circ., 84:67–74, 1991; McVeigh et al., "Noninvasive measurements of transmural gradients in myocardial strain with MR imaging," Radiology, 180(3):677–683, 1991; and Lugo-Olivieri et al., "The effects of ischemia on the temporal evolution of radial myocardial deformation in humans," Radiology, 193:161, 1994) to better understand the correlation of coronary artery disease with myocardial motion abnormalities (McVeigh et al., "Imaging asynchronous mechanical activation of the paced heart with tagged MRI," Magn. Res. Med., 39:507–513, 1998) to analyze cardiac activation patterns using pacemakers (Lima et al., "Segmental motion and deformation of transmurally infarcted myocardium in acute postinfarct period," Am. J. Physiol., 268(3):H1304–12, 1995) to understand the effects of treatment after myocardial infarction (Croisille et al., "Combined dobutamine stress 3D tagged and contrast enhanced MRI differentiate viable from non-viable myocardium after acute infarction and reperfusion," Circ., 92(8):1–508, 1995), and in combination with stress testing for the early detection of myocardial ischemia (Budinger et al., "Cardiac MR imaging: Report of a working group sponsored by the national heart, lung, and blood institute," Radiology, 208(3):573–576, 1998) Motivation for Cardiac MRI). Despite these successful uses, tagged MRI has been slow in entering into routine clinical use in part because of long imaging and postprocessing times, inadequate access to patients during imaging, and lack of understanding of MR processes and benefits by clinicians and their associates (Young et al., "Tracking and finite element analysis of stripe deformation in magnetic resonance tagging." IEEE Trans. Med. Imag., 14(3):413–421, September 1995).

Generally, the processing and analysis of tagged MR images can be divided into three stages: (1) finding the left ventricular (LV) myocardium in two-dimensional images; (2) estimating the locations of tag features within the LV wall; and (3) estimating strain fields from these measurements. Many known approaches rely on fully manual contouring of the endocardium and epicardium (Amini et al., "Coupled B-snake grids and constrained thin-plate splines for analysis of 2-D tissue deformations from tagged MRI," IEEE Trans. Med. Imag., 17(3):344–356, June 1998 and Guttman et al., "Tag and contour detection in tagged MR images of the left ventricle," IEEE Trans. Med. Image., 13(1):74–88, 1994), although semi-automated approaches have been proposed as well (T. S. Denny, "Identification of myocardial tags in tagged MR images without prior knowledge of myocardial contours," In J. Duncan and G. Gindi, editors, Proc. Inf. Proc. Med. Imag., pages 327–340, 1997). Recent work has also suggested fully automated contouring as well (Kerwin et al, "Tracking MR tag surfaces using a spatiotemporal filter and interpolator," Int. J. Imag. Sys. Tech., 10(2):128–142, 1999). In most cases, contouring results are required for the tag feature estimation stage, for which there are several semi-automated methods available (Amini et al., "Coupled B-snake grids and constrained thin-plate splines for analysis of 2-D tissue deformations from tagged MRI," IEEE Trans. Med. Imag., 17(3): 344–356, June 1998 and T. S. Denny, "Identification of myocardial tags in tagged MR images without prior knowledge of myocardial contours," In J. Duncan and G. Gindi, editors, Proc. Inf. Proc. Med. Imag., pages 327–340, 1997) and new algorithms that appear very promising for its full automation (Kerwin et al., "Tracking MR tag surfaces using a spatiotemporal filter and interpolator," Int. J. Imag. Sys. Tech., 10(2):128–142, 1999 and Moulton et al., "Spline surface interpolation for calculating 3-D ventricular strains from MRI tissue tagging," Am. J. Physiol. (Heart Circ. Physiol.), 270:H281–H297, 1996).

The third stage in tagged MR image processing, estimation of strain, is largely an interpolation and differentiation computation, and there are several methods described in the literature including finite element methods (McVeigh et al., "Noninvasive measurements of transmural gradients in myocardial strain with MR imaging." Radiology, 180(3):677–683, 1991; Amini et al., "Coupled B-snake grids and constrained thin-plate splines for analysis of 2-D tissue deformations from tagged MRI." IEEE Trans. Med. Imag., 17(3):344–356, June 1998; and O'Dell et al, "Three-dimensional myocardial deformations: Calculations with displacement field fitting of tagged MR images," Radiology, 195:829–835, 1995) a global polynomial fitting approach (Denney et al., "Reconstruction of 3-D left ventricular motion from planar tagged cardiac MR images: An estimation theoretic approach." IEEE. Trans. Med. Imag., 14(4):625–635, 1995), and a so-called model-free stochastic estimation approach (Denney, Jr. et al.,. "Model-free reconstruction of three-dimensional myocardial strain from planar tagged MR images," J. Magn. Res. Imag., 7:799–810, 1997 and Kerwin et al. "Cardiac material markers from tagged MR images," Med. Image Anal., 2(4):339–353, 1998). Methods to estimate tag surfaces (O'Dell et al., "Three-dimensional myocardial deformations: Calculations with displacement field fitting of tagged MR images," Radiology, 195:829–835, 1995; Amini et al., "Flexible shapes for segmentation and tracking of cardiovascular data," In Proc. IEEE Int. Conf. Image Proc., pages 5–9, IEEE Comp. Soc. Press, 1998; and Osman et al., "Direct calculation of 2D components of myocardial strain using sinusoidal MR tagging," In Proc. SPIE Med. Imag. Conf., February, 1998." San Diego) represent an intermediate stage between tag identification and strain estimation. Despite the apparent differences between these tagged MRI processing methods, they all share two key limitations: they are not fully-automated and they require interpolation in order to form dense strain estimates. The present invention addresses both of these concerns.

The present inventors have described a new approach to the analysis of tagged MR images, which is called harmonic phase (HARP) imaging (Osman et al., "Motion estimation from tagged MR images using angle images," In Proc. Int. Conf. Imag. Proc., Volume 1, pages 704–708. Comp. Soc. Press, 1998, Chicago; Osman et al., "Imaging heart motion using harmonic phase MRI," October 1998." submitted; and Shinnar et al., "Inversion of the Bloch equation," J. Chem. Phys., 98(8):6121–6128. April 1993). This approach is based on the use of SPAMM tag patterns (Axel et al., "MR imaging of motion with spatial modulation of magnetization," Radiology, 171:841–845, 1989), which amplitude modulate the underlying image, producing an array of spectral peaks in the Fourier domain. Each of these spectral peaks carry information about a particular component of tissue motion. This information can be extracted using phase demodulation methods. In Shinnar et al, "Inversion of the Bloch equation," J. Chem. Phys., 98(8)

:6121–6128, April 1993, there is described what might be referred to as single-shot HARP image analysis techniques: reconstructing synthetic tag lines, calculating small displacement fields, and calculating Eulerian strain images. These methods require data from only a single phase (time-frame) within the cardiac cycle, but are limited because they cannot calculate material properties of the motion. In the present invention, the methods may employ image sequences—CINE tagged MR images—which preferably involve both a material point tracking technique and a method to use these tracked points to calculate Lagrangian strain, including circumferential and radial strain.

The methods proposed in the present invention are fast and fully-automated, and use data that can be collected rapidly. These methods apply only directly to two-dimensional images. As a result, the estimated motion quantities should be thought of as "apparent" motion as they represent the projection of 3-D motion onto a 2-D plane. Although the methods can be extended to 3-D images, dense data acquisition methods would be employed. The present methods should have immediate clinical impact because the methods are automatic and because circumferential strain is particularly important in the analysis of left ventricular motion.

Figure 8A:
FIG. 8(a) shows a magnetic resonance image with horizontal SPAMM tags.

Considering first the SPAMM tagging methods, let I(y,t) represent the intensity of a tagged cardiac MR image at image coordinates y=[$y_1$ $y_2$]$^T$ and time t. A typical image showing abnormal motion of a canine heart is shown in FIG. 8(a). The left ventricle (LV) looks like an annulus in the center of the image. The effect of tagging can be described as a multiplication of the underlying image by a tag pattern. The pattern appearing in FIG. 8(a) is a one-dimensional SPAMM tag pattern (grid) (Axel et al., "*MR imaging of motion with spatial modulation of magnetization,*" *Radiology,* 171:841–845, 1989), which can be written as a finite cosine series having a certain fundamental frequency (M. E. Gurtin, "*An Introduction to Continuum Mechanics,*" Academic Press, Inc., 1981). Multiplication by this pattern causes an amplitude modulation of the underlying image, which replicates its Fourier transform into the pattern shown in FIG. 8(b). The locations of the spectral peaks in Fourier space are integer multiples of the fundamental tag frequency determined by the SPAMM tag pulse sequence.

A 2-D pattern of spectral peaks can be generated by using a 2-D SPAMM tag pattern. The methods of the present invention can be employed in this case as well.

Static HARP imaging (Osman et al., "*Imaging heart motion using harmonic phase MRI,* October 1998. "submitted and Sinnar et al., "*Inversion of the Bloch equation,*" *J. Chem. Phys.,* 98(8):6121–6128, April 1993) uses a bandpass filter to isolate the k-th spectral peak centered at frequency $\omega_k$-typically the lowest harmonic frequency in a certain tag direction. The bandpass filter usually has an elliptical support with edges that roll off smoothly to reduce ringing. The contour drawn in FIG. 8(b)—a circle in this case—represents the −3 dB isocontour of the bandpass filter used to process this data. Once the filter is selected, the same filter is used in all images of the sequence, except that a rotated version is used to process the vertical tagged images. Selection of the filters for optimal performance is discussed in Shinnar et al., "*Inversion of the Bloch equation,*" *J. Chem. Phys.,* 98(8):6121–6128, April 1993. The inverse Fourier transform of the bandpass region yields a complex harmonic image which is given by $$I_k(y,t)=D_k(y,t)e^{j\phi_k(y,t)} \quad (15)$$

where $D_k$ is called the magnitude image and $\phi_k$ is called the phase image. The use of $I_k$ in Equation 15 is the same as $\psi$k in Equation 10.

Figure 8B:
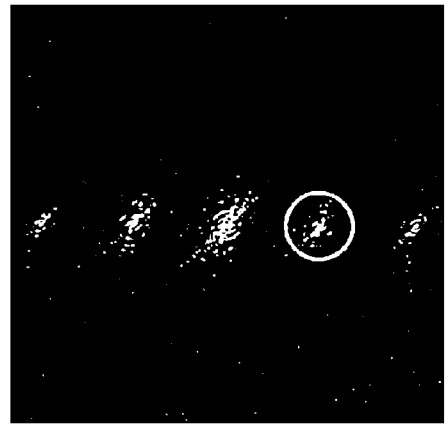
FIG. 8(b) shows the magnitude of the Fourier transform of the image of FIG. 8(a).
Figure 8C:
FIG. 8(c) shows a complex image produced by extracting the spectral peak inside the circle of FIG. 8(b) illustrative of the magnitude.

The magnitude image $D_k$(y,t) reflects both the changes in geometry of the heart and the image intensity changes caused by tag fading. FIG. 8(c) shows the harmonic magnitude image extracted from FIG. 8(a) using the filter in FIG. 8(b). It basically looks like the underlying image except for the blurring caused by the filtering process. Because of the absence of the tag pattern in the harmonic magnitude image, it can be used to provide a segmentation that distinguishes tissue from background. A simple threshold can be employed to provide a crude segmentation, where the threshold is selected manually at both end-diastole and end-systole and linearly interpolated between these times.

The phase image $\phi$(y,t) provides a detailed picture of the motion of the myocardium in the direction of $\omega_k$. In principle, the phase of $I_k$ can be computed by taking the inverse tangent of the imaginary part divided by the real part. Taking into account the sign of $I_k$, the unique range of this computation can be extended to [−π,π)—using the atan2 operation in C, Fortran, or MATLAB, for example. Still, this produces only the principal value not the actual phase, which takes its values on the whole real line in general. This principal value can be denoted by $a_k$(y,t); it is mathematically related to the true phase of $I_k$ by $$a_k(y,t)=W(\phi_k(y,t)), \quad (16)$$

where the nonlinear wrapping function is given by $$W(\phi)=\text{mod}(\phi+\pi, 2\pi)-\pi.$$

Figure 8D:
FIG. 8(d) is illustrative of the phase thereof.

Either $a_k$ or $\phi_k$ might be called a harmonic phase (HARP) image. This expression will generally be employed for $a_k$ as unlike $\phi_k$, it can be directly calculated and visualized from the data. Where the two might be confused, however, $\phi_k$ will be referred to as the harmonic phase and $a_k$ as the harmonic phase angle. The HARP angle image corresponding to the spectral peak outlined in FIG. 8(b) is shown in FIG. 8(d). For clarity, it is displayed on a mask created using a crude segmentation of the magnitude image in FIG. 8(c).

Careful inspection of the HARP image in FIG. 8(d) reveals intensity ramps in the vertical direction interrupted by sharp transitions caused by the wrapping artifact. The locations of these transitions are very nearly coincident with the tag lines in FIG. 8(a), and both reflect myocardial motion occurring during systolic contraction. The intensity ramps in HARP images actually contain denser motion information than what is readily apparent in the original image. For example, calculated isocontours of HARP angle images can produce tag lines throughout the myocardium with arbitrary separation (Osman et al., "*Inversion of the Bloch equation.*" *J. Chem. Phys.,* 98(8):6121–6128, April 1993). The underlying principle is that both the harmonic phase and the HARP angle are material properties of tagged tissue; therefore, a material point retains its HARP angle throughout its motion. This is the basis for HARP tracking of motion.

Figure 9A:
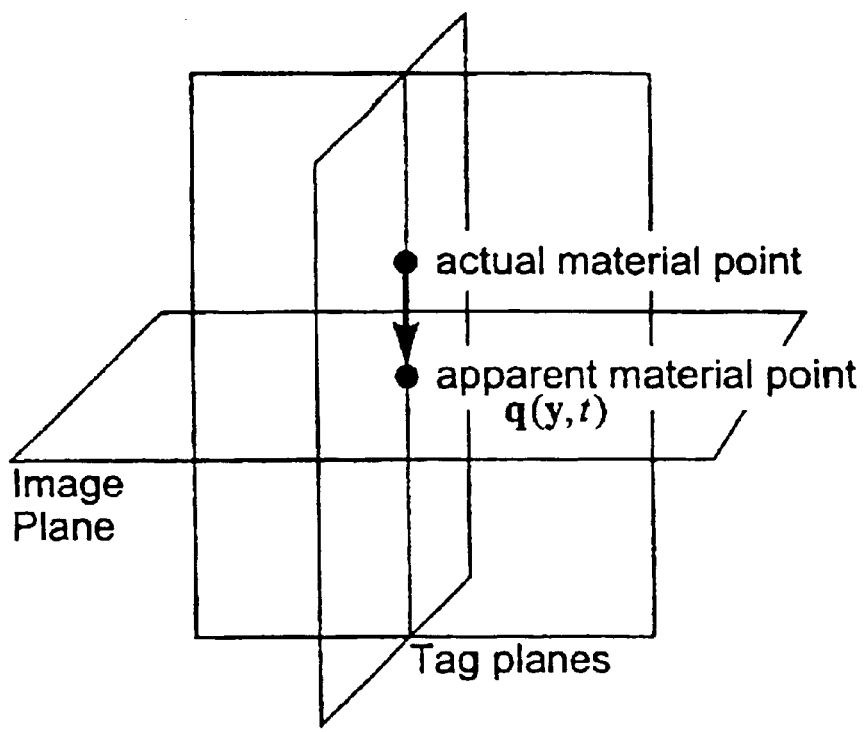
FIG. 9(a) illustrates schematically tag planes at the end-diastole and FIG. 9(b) illustrates distortion of the tag planes resulting from motion.

Turning now to the matter of "apparent" motion in tagging pulse sequences, the tag gradients are usually applied in the plane of the image. In this case, a tag line appearing in an image at end-diastole is actually part of a tag plane that is orthogonal to the image plane, as shown in FIG. 9(a). As harmonic phase is a material property, the set of points having the same harmonic phase $\phi$ at end-diastole is also a plane orthogonal to the image plane, and can be considered to be just another type of tag plane. The set of points having the same HARP angle α at end-diastole comprises a collection of parallel planes rather than just a single plane. This creates a problem in HARP tracking which we address in the following section. To describe apparent motion, the unique association afforded by the harmonic phase $\phi$ is considered.

Figure 9B:
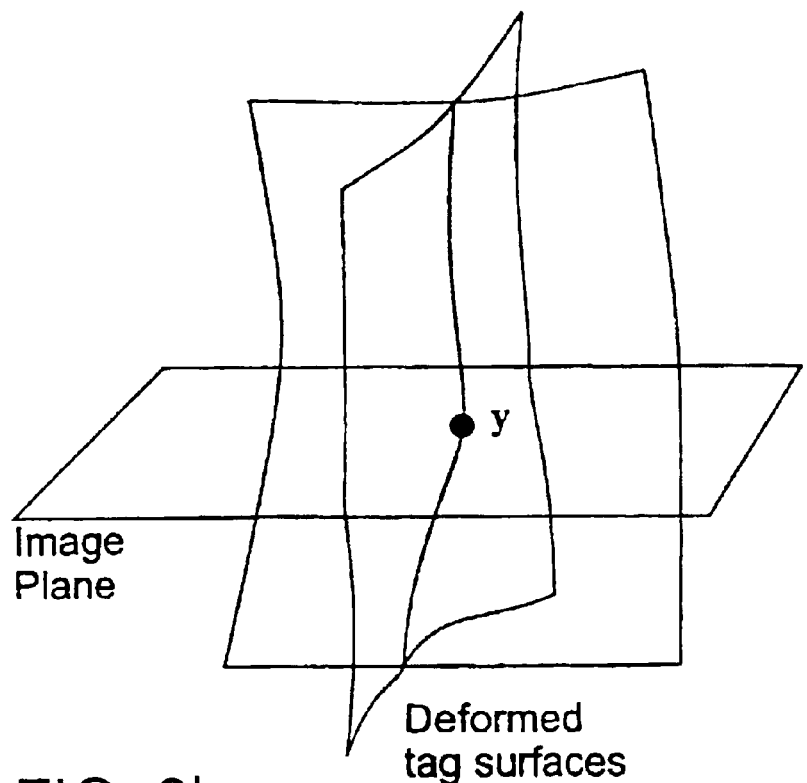

Given both horizontal and vertical tagged images, it is clear from FIG. 9(a) that the set of points having the same two harmonic phases at end-diastole comprises a line orthogonal to the image plane intersecting at a single point. As depicted in FIG. 9(b), the tag planes distort under motion, causing this line to distort into a curve. Under modest assumptions about the motion, this curve will still intersect the image at a single point. This point can then be uniquely associated with the corresponding point at end-diastole representing an apparent motion within the image plane.

The apparent motion can be described mathematically using an apparent reference map denoted by $q(y,t)$. This function gives the point within the image plane where y apparently was at end-diastole (in the sense that is has the same two harmonic phases). It is clear from FIG. 9 and can be shown that $q(y,t)$ is the orthogonal projection of the true 3-D material point location at end-diastole onto the image plane. Although calculation of apparent 2-D motion has its limitations, it does have a very precise relationship to the true three-dimensional motion. The motion quantities derived from apparent motion, such as strain, can be related to the true 3-D quantities in equally rigorous fashion.

The HARP processing of CINE-tagged magnetic resonance images involves (1) tracking the apparent motion of material points in an image plane and (2) calculating Lagrangian strain from such tracked points. To arrive at compact equations, vector notation is used. In particular, the vectors $\phi=[\phi_1\ \phi_2]^T$, and $a=[a_1\ a_2]^T$ are defined to describe pairs of harmonic phase images and HARP angle images, respectively, of the harmonic images $I_1$ and $I_2$.

In HARP tracking, as harmonic phase cannot be directly calculated, its principal value, the HARP angle, is employed in computations. An immediate consequence is that there are many points in the image plane having the same pair of HARP angles. For a given material point with two HARP angles, only one of the points sharing the same HARP angles in a later image is the correct match, i.e., it also shares the same pair of harmonic phases. If the apparent motion is small from one image to the next, then it is likely that the nearest of these points is the correct point. The present method tracks apparent motion through a CINE sequence of tagged MR images. Assume a material point located at $y_m$ at time $t_m$. If $y_{m+1}$ is the apparent position of this point at time $t_{m+1}$ then $$\phi(y_{m+1}, y_{m+1})=\phi(y_m, t_m) \tag{18}$$

This relationship provides the basis for tracking $y_m$ from time $t_m$ to time $t_{m+1}$. It is desired to find y that satisfies $$f(y)=\phi(y,t_{m+1})-\phi(y_m,t_m)=0 \tag{19}$$

and then set $y_{m+1}=y$. Finding a solution to Equation (19) is a multidimensional, nonlinear, root finding problem, which can be solved iteratively using the Newton-Raphson technique. After simplification, the Newton-Raphson iteration is $$y^{(n+1)}=y^{(n)}-|\nabla\phi(y^{(n)}, t)|^{-1}|\phi(y^{(n)}, t_{m+1})-\phi(y_m,t_m)| \tag{20}$$

There are several practical problems with the direct use of Equation (20). The first problem is that $\phi$ is not available, and a must be used in its place. Fortunately, it is relatively straightforward to replace the expressions involving $\phi$ with those involving a. It is clear from Equation (16) that the gradient of $a_k$ is the same as that of $\phi_k$ except at a wrapping artifact, where the gradient magnitude is theoretically infinite—practically very large (see also FIG. 8(d)). It is also apparent from Equation (16) that adding $\pi$ to $a_k$ and re-wrapping shifts the wrapping artifact by ½ the spatial period, leaving the gradient of this result equal to that of $\phi_k$. As a result, the gradient of $\phi_k$ is equal to the smaller (in magnitude) of the gradients of $a_k$ and $W(a_k+\pi)$. Formally, this can be written as $$\nabla\phi=\nabla^* a \tag{21}$$

where $$\nabla^* a \equiv \begin{bmatrix} \nabla^* a_1 \\ \nabla^* a_2 \end{bmatrix} \text{ and} \tag{22}$$

$$\nabla^* a_k \equiv \begin{cases} \nabla a_k & \|\nabla a_k\| \le \|\nabla W(a_k+\pi)\| \\ \nabla W(a_k+\pi) & \text{otherwise} \end{cases} k=1,2. \tag{23}$$

A second problem with the use of Equation (20) is calculation of the expression $\phi(y^{(n)},t_{m+1})-\phi(y_m,t_m)$, which appears to be nearly impossible as we do not know the phase itself, but only its wrapped version, the harmonic phase. However, provided that $|\phi_k(y^{(n)},t_{m+1})-\phi_k(y_m,t_m)|<\pi$ for $k=1, 2$—a small motion assumption—it is straightforward to show that $$\phi(y^{(n)},t_{m+1})-\phi(y_m,t_m)=W(a(y^{(n)},t_{m+1})-a(y_m,t_m)). \tag{24}$$

Substituting Equation (21) and Equation (24) into Equation (20) provides the formal solution $$y^{(n+1)}=y^{(n)}-|\nabla a^*(y^{(n)},t)|^{-1}W(a(y^{(n)},t_{m+1})-a(y_m,t_m)) \tag{25}$$

There are several issues to consider in the implementation of an algorithm based on Equation (25). First, because of the phase wrapping, the solution is no longer unique; in fact, one can expect a solution satisfying $a(y,t_{m+1})=a(y_m,t_m)$ approximately every tag period in both directions. It is, therefore, desirable both to start with a "good" initial point and to restrain the step size to prevent jumping to the wrong solution. Accordingly, it is desirable to initialize the algorithm at $y^{(0)}=y_m$ and limit our step to a distance of one pixel. A second issue has to do with the evaluation of $a(y,t_{m+1})$ for arbitrary y. Straight bilinear interpolation would work ordinarily; but in this case the wrapping artifacts in a cause erroneous results. To prevent these errors we perform a local phase unwrapping of a in the neighborhood of y, bilinearly interpolate the unwrapped angle, and then wrap the result to create an interpolated HARP angle. A final consideration is the stopping criterion. Two criteria are employed: (1) that the calculated angles are close enough to the desired target HARP vector or (2) that an iteration count is exceeded.

Putting all these considerations together, one can readily define an algorithm that with track a point in one time frame to its apparent position in the next time frame. It is useful to cast this algorithm in a more general framework in order to make it easier to define the HARP tracking algorithm which tracks a point through an entire sequence of images. Accordingly, the method considers $y_{init}$ to be an initialization from which the search is started, and $a^*$ to be a target HARP vector. To track point $y_m$ at time $t_m$ to its apparent position in time $t_{m+1}$, one sets $y_{init}=y_m$, $a^*=a(y_m,t_m)$, picks a maximum iteration count N, and then runs the following algorithm:

Algorithm 1 (HARP Targeting) Let n=0 and set $y^{(0)}=y_{init}$
1. If n>N or $\|W(a(y^{(n)},t_{m+1})-a^*\|<\in$ then the algorithm terminates with $\hat{y}_{m+1}=y^{(n)}$ 2. Compute a step direction $$v^{(n)}=-[\nabla^* a(y^{(n)},t)]^{-1} W(a(y^{(n)},t_{m+1})-a^*)$$

using an appropriate interpolation procedures.

3. Compute a step size $$\alpha^{(n)} = \min\left\{\frac{1}{\|v^{(n)}\|}, 1\right\}$$

4. Update the estimate $$y^{(n+1)}=y^{(n)}+\alpha^{(n)}v^{(n)}$$

5. Increment n and go to step 1.

To track a point through a sequence of images, HARP targeting is successfully applied to each image in the sequence. A preferred approach to finding the correct apparent motion is to keep the target HARP vector the same throughout the entire sequence—equal to that of the original point—but to initialize HARP targeting to the previous estimated apparent position in the sequence. This produces a succession of points having the same HARP angles and generally avoids jumping to the wrong solution by keeping the initial point used in HARP targeting near to the desired solution. To formally state this algorithm, assume that one wants to track $y_j$ at time $t_j$ through all images at times $t_{j+1}$, $t_{m+2}$, ....

HARP tracking is given by the following algorithm:
Algorithm 2 (HARP Tracking) Set $a^*=a(y_j,t_j)$, $\hat{y}_j=y_j$, and m=j.
Choose a maximum iteration threshold N (for HARP targeting).
1. Set $y_{init}=\hat{y}_m$.
2. Apply Algorithm 1 (HARP targeting) to yield $\hat{y}_{m+1}$
3. Increment m and go to step 1.

It should be noted that HARP tracking can be used to track points backwards in time in exactly the same way as forwards. Therefore, it is possible to specify a point in any image at any time and track it both forward and backward in time, giving a complete trajectory of an arbitrary point in space and time.

In determining Lagrangian strain, assume that the reference time t=0 is at end-diastole. HARP tracking allows one to track a material point q at t=0 to its location (all position quantities in this section refer to "apparent" location) y at time t (at least for the collection of available image times). This provides an estimate of the motion map y (q,t). Using y(q,t) one can estimate the deformation gradient tensor $F=\nabla_q y(q,t)$ at any material point q and time t using finite differences. By computing the deformation gradient, other motion quantities of interest are readily calculated (Atalar et al., "*Optimization of tag thickness for measuring position with magnetic resonance imaging,*" IEEE Trans. Med. Imag., 13(1):152–160, 1994). The more powerful application of HARP tracking is revealed in a somewhat simpler calculation within a semi-automated analysis, which follows.

Consider the motion of two material points $q_i$ and $q_j$. The unit elongation or simple strain is given by $$e = \frac{\|y(q_i, t_m) - y(q_j, t_m)\|}{\|q_i - q_j\|} - 1 \quad (26)$$

This quantity is zero if the distance between the points remains unchanged, negative if there is shortening, and positive if there is lengthening. To measure circumferential strain at any location within the left ventrical wall one simply places two points along a circle centered at the LV long axis. To measure radial strain, one simply places two points along a ray emanating from the long axis. In either case, the strain is measured by tracking the two points using HARP tracking and calculating e. It must be emphasized again that the location of these points need not be at "tag intersections" or even pixel locations as HARP tracking is fundamentally capable of tracking arbitrary points in the image. This measure of strain has two advantages over the dense calculation of the Lagrangian (or Eulerian strain) tensor. First, it is extremely fast as only two points need to be tracked instead of the entire image (or region-of-interest). Second, the points are generally placed farther apart than a single pixel, so the elongation calculation is intrinsically less sensitive to noise.

Figure 10:
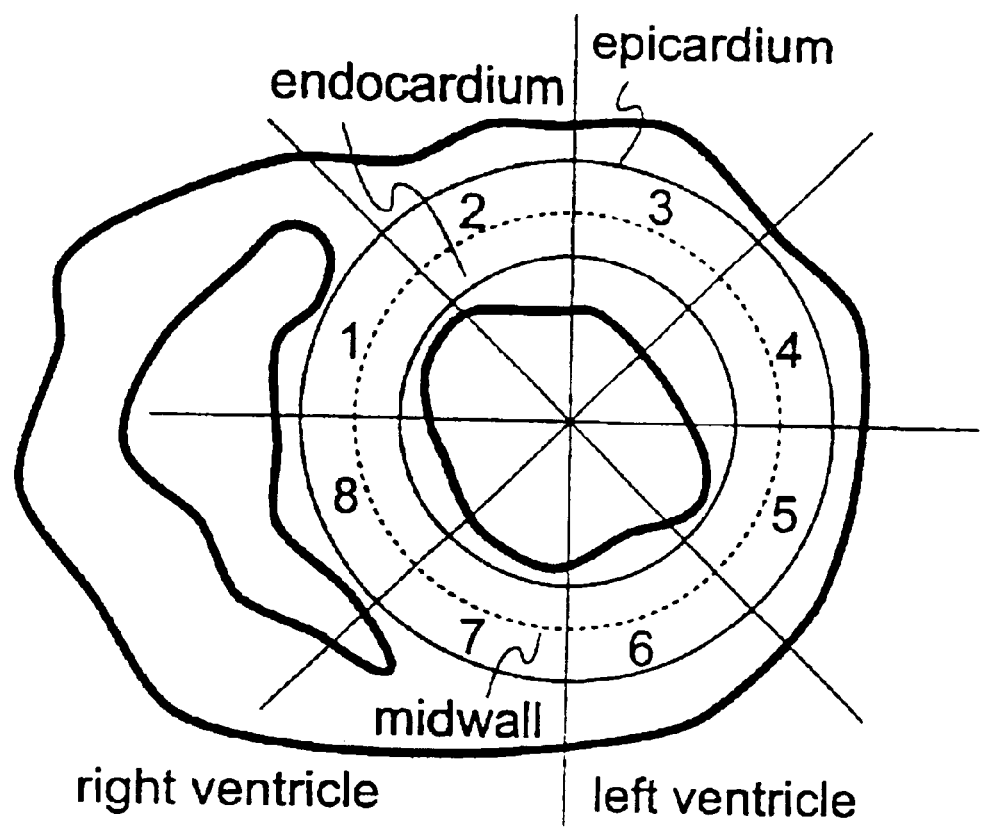
FIG. 10 is a schematic illustration of concentric circles superimposed upon an illustration of a heart left ventricle wall and eight octants.

To exploit these advantages, an approach was implemented that tracks points on concentric circles within the myocardium and calculates regional radial and circumferential Lagrangian strain. A simple user interface allows the placement of three concentric circles within the LV wall, as shown in FIG. 10. These circles are manually placed by first clicking on the center of the ventricle—the location of the long axis—and then dragging one circle to the epicardium and another to the endocardium. The third circle is automatically placed halfway between these two. Usually the circles are defined on the end-diastolic image, but sometimes it is easier to define them using the end-systolic image because the cross section of the LV may be more circular. Sixteen equally-spaced points are automatically defined around the circumference of each circle, and all 48 points are tracked (forward or backward in time) using Algorithm 2 (HARP tracking).

Strain is computed by measuring the change in distance between neighboring points through the time frames. Regardless of whether the circles were defined at end-diastole, at end-systole, or at nay time in between, the end-diastolic image frame is used as the material reference. The change in distance between points on the same circle corresponds to circumferential strain. The change in distance between radially-oriented points corresponds to radial strain. Because there are three concentric circles, one can calculate endocardial, epicardial, and midwall circumferential strain and endocardial and epicardial radial strain. To obtain some noise reduction and for simplicity in presentation, the circles were divided into eight octants and the computed strains were averaged in each of these octants. By convention, the octants were numbered in the clockwise direction starting from the center of the septum as shown in FIG. 10. The resulting strains are plotted as a function of both time and octant, yielding a spatio-temporal display of cardiac performance within a cross section.

The above procedure involves tracking a collection of points, which ordinarily can be successfully accomplished by applying Algorithm 2 to each point independently. In some cases, however, large myocardial motion or image artifacts may cause a point to converge to the wrong target (tag jumping) at some time frame, causing erroneous tracking in successive frames as well. The present invention employs a refinement procedure that uses one or more correctly tracked points to correct the tracking of erroneously tracked points.

As stated, Algorithm 2 is initialized at the previous estimated position of the point being tracked. If the in-plane motion between two time frames is very large, however, this initial point may be too far away from the correct solution and it will converge to the wrong point. Refinement is based on the systematic identification of better initializations for Algorithm 2. Suppose it can be verified that one point on a given circle has been correctly tracked throughout all frames. In one experiments, we have always found such a point on the septum, where motion is relatively small. This point is employed as an "anchor" from which the initializations of all other points on the circle and, if desired, all points on all three circles can be improved and the overall collective tracking result refined.

Starting with the correctly tracked anchor, a sequence of points separated by less than one pixel on a line segment connecting the anchor with one of its neighbors on the circle is defined. Suppose the anchor is tracked to point y at some particular time. As by assumption this point is correctly tracked, the correct tracking result of a point near to the anchor will be near y. Accordingly, y is employed as the initial point in Algorithm 2 to track the first point in the sequence. This result is then employed as the initial point for the second point in the sequence, and so on. Upon arriving at the anchor's first neighbor on the circle, there will have been no opportunity to converge to the wrong result and jump a tag. The neighbor now serves as a new anchor, and the procedure is repeated for the next neighbor on the circle, until all the points on the circle have been tracked.

Refinement may be employed to "bridge" circles along a radial path and successively correct all three circles. Generally, tag jumping errors occur only in the free wall, and as refinement is computationally demanding, its operation is generally restricted to a single circle at a time. If desired, as a check, the circle can be completed by tracking all the way around and back to the original anchor. If the result is different, then there is a gross error, and it is desirable to redefine the circle. Tag fading or other image artifacts can occasionally cause this type of gross error, but it is more likely to be caused by out-of-plane motion. Out-of-plane motion causes the actual tissue being imaged to change. In this case, it is possible that there is no tissue in the image plane carrying the harmonic phase angles corresponding to the point being tracked. In summary, the tags may disappear, and the HARP tracking algorithm will simple converge to another point having the correct HARP angles. Because of the particular relationship between the motion and geometry of the left ventrical, this is not a significant problem. As the problem is most likely to occur near the boundaries of the left ventrical, the main limitation it imposes is that one generally must not place the circles very near to the epicardium or endocardium.

EXAMPLES

In order to confirm the effectiveness of the methods of the present invention, experiments were performed on both normal and abnormal hearts with the tests involving both canines and human beings. An abnormally paced canine data set was obtained as was data from a normal human heart under dobutamine stress. Quantitative comparisons between HARP tracking and a prior art well-accepted tag tracking method are made.

EXAMPLE 1

To demonstrate the capabilities of HARP tracking, a set of tagged images of an electrically paced canine heart were used. These data were previously used in a study of cardiac motion under electrically paced activation using tagged magnetic resonance imaging and analysis techniques. A complete description of the experimental protocol and their results are given in Lima et al., "*Segmental motion and deformation of transmurally infarcted myocardium in acute postinfarct period.*" *Am. J. Physiol.*, 268(3):H1304–12, 1995. Although the present results yield only apparent motion and strain on a single cross-section rather than giving a complete 3-D description, the results obtained here are very nearly the same as those in Lima et al., but are generated in only a fraction of the time. This provides the benefit of accurate, rapid results through use of the methods of the present invention.

A pacing lead was placed in the left ventricular basal free wall of a canine heart. Magnetic resonance imaging was performed on a standard 1.5 T scanner with software release 4.7 (General Electric Medical Systems, Milwaukee, Wis.). A 6 ms SPAMM pulse sequence was used to produce a tag pattern in the myocardium comprising parallel plane saturation bands separated by 5.5 mm in the image plane. The tagging pulse sequence was triggered with a signal from the pacer, and the imaging sequence started 3 ms after the tagging pulses were completed. The image scanning parameters were: TR=6.5 ms, TE=2.1, readout-bandwidth=±3.2 kHz, 320 mm field of view, 256×96 acquisition matrix, fractional echo, two readouts per movie frame and 6-mm slice thickness.

Figure 11:
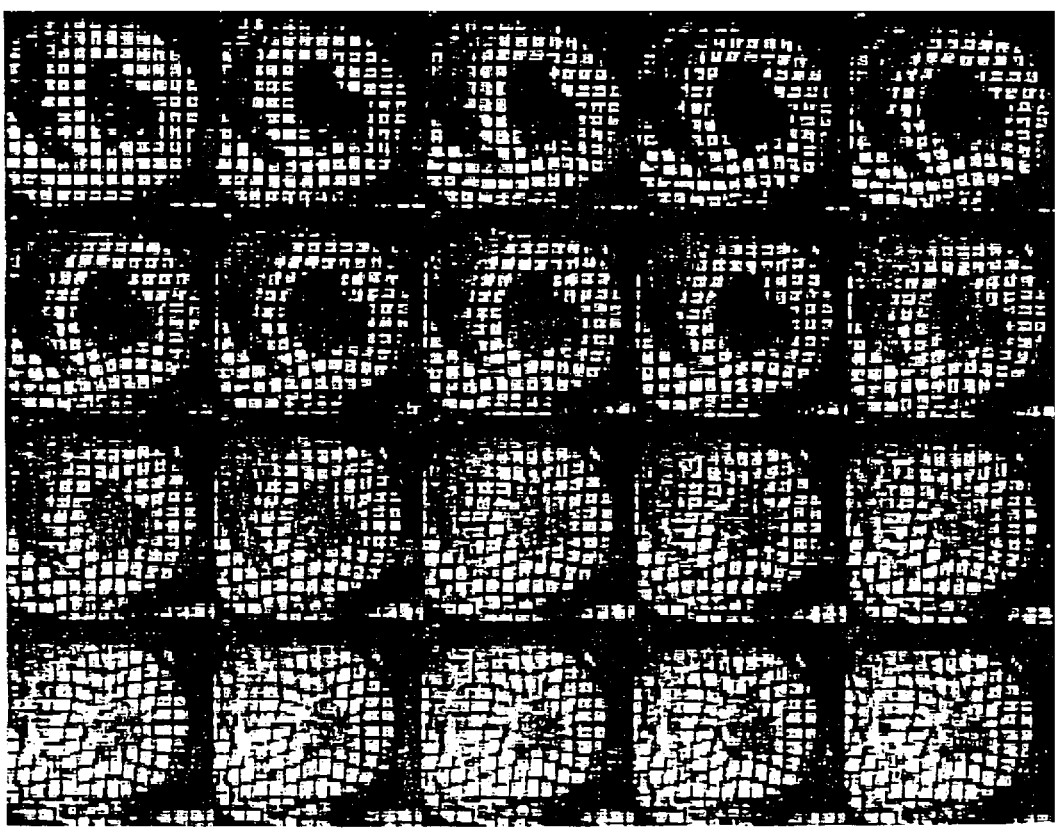
FIG. 11 illustrates a sequence of tagged magnetic resonance images of a paced canine heart created by multiplying the vertical and horizontal tag images to provide a grid. The images are twenty time frames depicting the motion of a paced canine heart from end-diastole shown at the top left to end-systole shown at the bottom right.
Figure 12A:
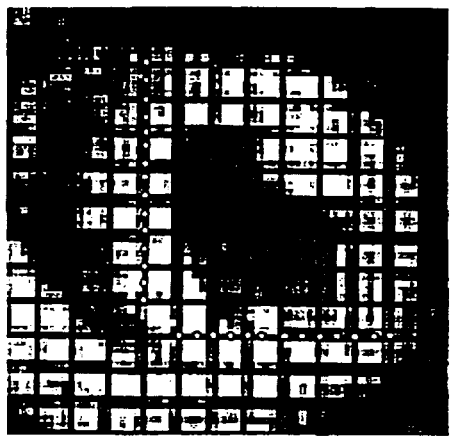
FIG. 12(a) shows manually selected points at the time frame 1 tracked through time and displayed respectively at time frame 5 in FIG. 12(b), time frame 10 in FIG. 12(c), and time frame 20 in FIG. 12(d).
Figure 12B:
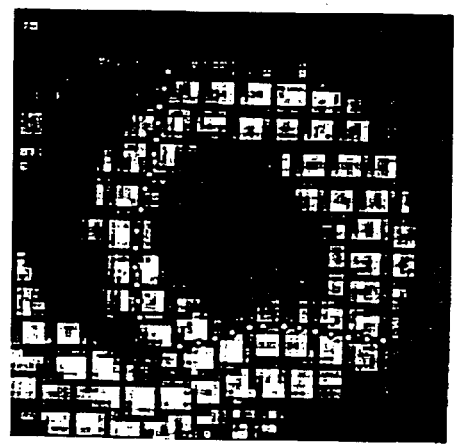
Figure 12C:
Figure 12D:
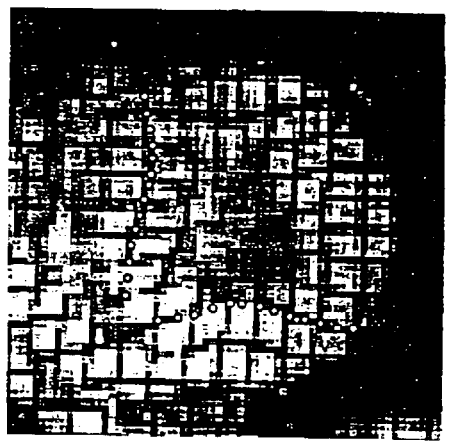
Figure 13A:
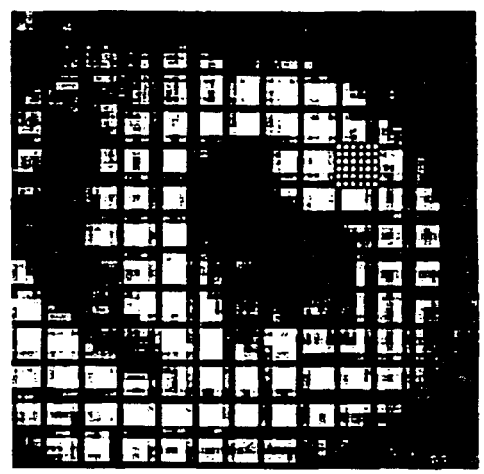
FIG. 13(a) illustrates the heart at end-diastole showing the position of the densely picked points and an enlargement of the track material points at time frame 1 in FIG. 13(b), time frame 5 in FIG. 13(c), time frame 10 in FIG. 13(d), and time frame 20 in FIG. 13(e).
Figure 13B:
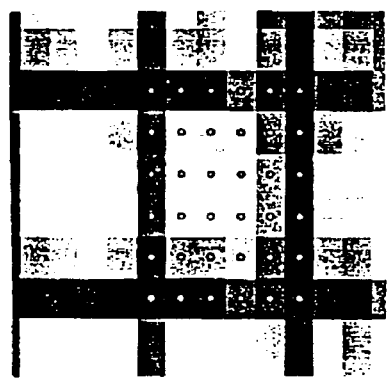
Figure 13C:
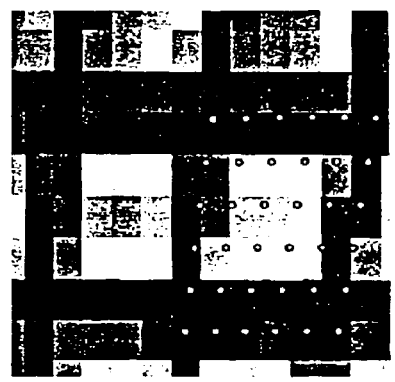
Figure 13D:
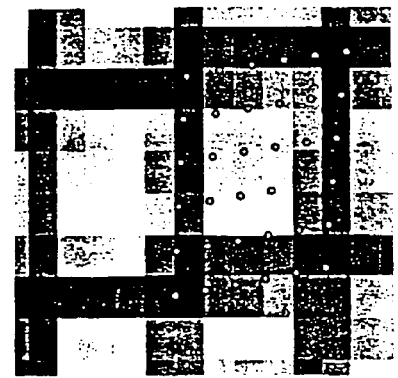
Figure 13E:
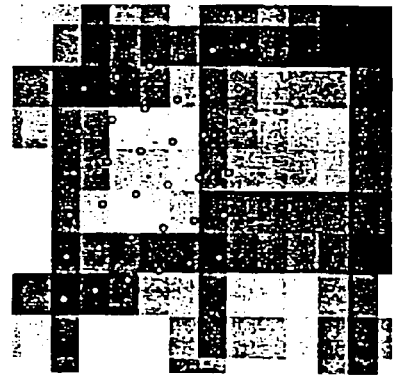

Two sequences of 20 tagged MR short-axis images, one with horizontal tags and the other with vertical tags, were acquired at 14 ms intervals during systole. The images were acquired during breath-hold periods with segmented k-space acquisition. The images acquired in a basal plane, near the location of the pacing lead were used. FIG. 11 shows the resulting images cropped to a region of interest around the LV for visualization purposes. Strong early contraction can be seen near the pacing lead at about 5 o'clock. The septal wall is seen to bow outward in frames 4–8, an abnormal motion called pre-stretching caused by a delay in the electrical activation signal to the septal region. After this, the entire LV myocardium experiences continued contraction throughout systole in nearly normal fashion.

In HARP tracking, the HARP images were computed from the horizontal tagged image sequence using the bandpass filter depicted in FIG. 8(*b*); a 90-degree rotated version of this filter was used to compute the vertical HARP images. To demonstrate HARP tracking (Algorithm 2), two tag lines were selected, one vertical and one horizontal, and manually selected a collection of tag points on each. The locations of these points are their individually tracked positions at three later times are shown in FIG. 12. With just one exception, all the points were tracked where one would expect to see them even after considerable tag fading. In particular, both the inward "bowing" of normal contraction and the outward "bowing" of the abnormal pre-stretching motion are captured very well by HARP tracking. The only incorrectly tracked point can be seen at the top of the image in FIG. 12(*d*). Careful examination of the images shows that out-of-plane motion has caused the horizontal tag line present at the top of the LV in the first time frame to disappear over time. This type of problem while not solved by refinement, can be avoided by choosing points that are not very near to the myocardial boundaries.

To show that HARP tracking is not limited to points on tag lines and to show its potential for calculating strain tensors, a 5 by 5 grid of points separated by one pixel (1.25 mm) was placed in a region bounded by four tag lines in the anterior lateral side of the LV, as shown in FIG. 13(*a*). These points were independently tracked through the full image sequence; FIGS. 13(*b*)–(*c*) shows enlarged pictures of their positions at time frames 1, 5, 10, and 20. Subpixel resolution of tracked points are clearly manifested in the later images, and the underlying local pattern of strain is clearly visible. The pronounced progression of the grid's shape from a square to a diamond demonstrates very clearly both the radial thickening and circumferential shortening present in normal cardiac motion. It is evident from the regularity of the tracked points that finite differences could be easily used to compute a strain tensor from this data. From this, various quantities related to motion can be computed including regional area changes and directions of principle strains.

Next, the regional Lagrangian strain was computed using the procedure de-scribed after Algorithm 2. Using a user interface, epicardial and endocardial circles were defined. As the LV looks most circular at end-systole, the last image in FIG. 11 was employed to define these circles. The resulting three circles and the defined octants are shown in FIG. 14(a). Sixteen points on each circle were tracked backwards in time to end-diastole, resulting in the shapes shown in FIG. 14(b). The entire sequence of deformed states is shown in FIG. 14(c). From this sequence, it is seen that the shape of the LV cross-section starts somewhat elongated, but rapidly become circular and then undergoes a mostly radial contraction. It is easy to confirm that there are no incorrectly tracked points in FIG. 14 because such tag jumps would yield a very distorted contour in one or more time frames.

Figure 15A:
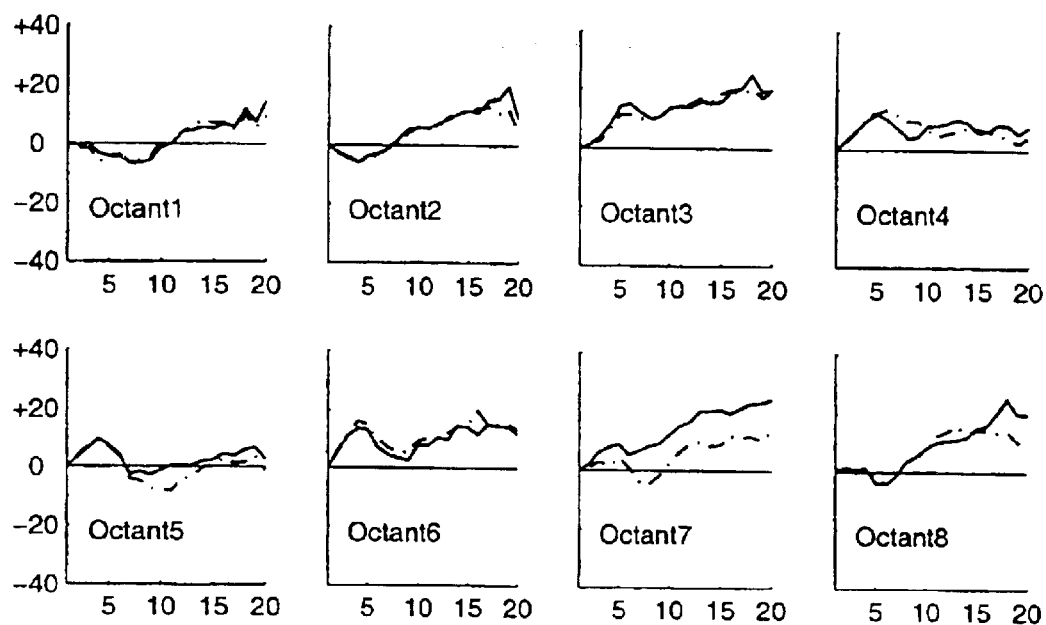
FIG. 15(a) illustrates the time evolution of epicardial (dot-dashed) and endocardial (solid) radial strain in each octant.

Lagrangian strain profiles were computed for the tracked points depicted in FIG. 14(c) as described hereinafter in Algorithm 2. The temporal evolution of radial strain in each octant is shown in FIG. 15(a). Positive values indicate myocardial thickening while the negative values indicates thinning. Early myocardial thickening is apparent only in octants 3–6, while octants 8, 1, and 2, show thinning. This is a direct expression of both the early strong contraction taking place in the myocardium nearest the pacing lead and the pre-stretching of the myocardium on the opposite wall. During time frame 5–10 the myocardium nearest the pacing lead in octants 5–7 relax before contracting a second time toward the strongest radial thickening at end-systole. There is very little apparent difference between epicardial and endocardial radial strain except in quadrant 7, where the endocardial thickening is larger.

Figure 15B:
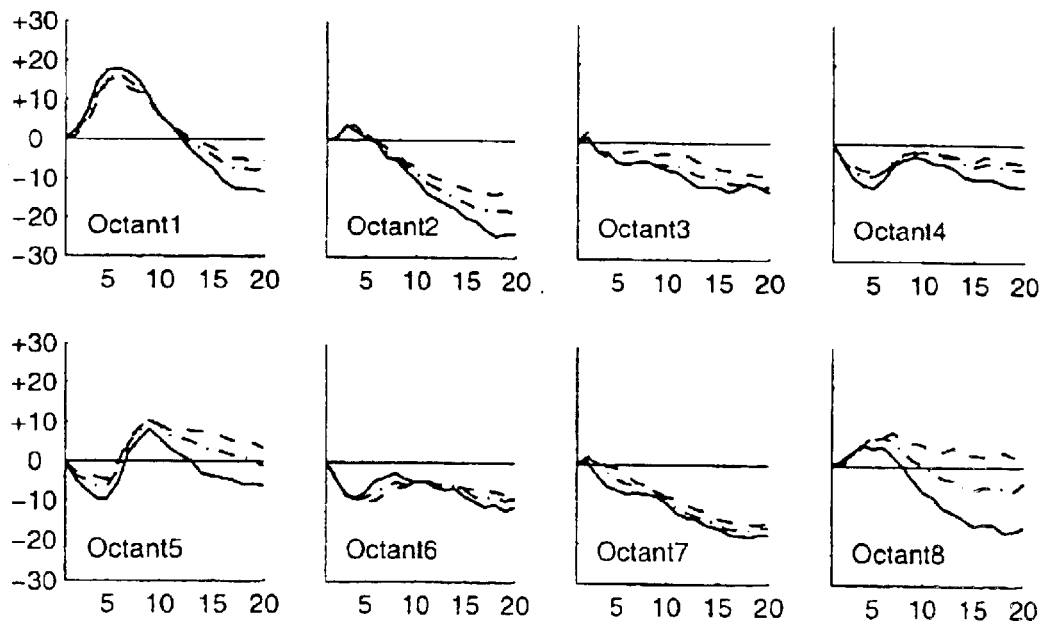
FIG. 15(b) illustrates the time evolution of epicardial (dashed), midwall (dot-dashed), and endocardial (solid) circumferential strain in each octant.

FIG. 15(b) shows the temporal evolution of circumferential strain within each octant. Positive values indicate stretching in the circumferential direction while the negative values indicate contraction. These plots show the same general behavior as in the radial strain profiles. Early contraction in octants 4–6 is seen as a shortening, while octants 8, 1, and 2 show a significant stretching during this same period. After some interval, all myocardial tissues exhibit contractile shortening. These plots also demonstrate a consistently larger endocardial shortening than the midwall which had more shortening than the epicardium. This agrees with the known behavior of the left ventricular myocardium during contraction (Clark et al., "*Circumferential myocardial shortening in the normal human left ventricle,*" Circ., 84:67–74, 1991).

EXAMPLE 2

This example involves the use of HARP tracking of the cardiac motion of a normal human male volunteer age 27 undergoing a dobutamine-induced (5 µg/kg/min) cardiac stress. This example includes the very rapid motion of this heart under dobutamine stress and the use of HARP refinement to correct incorrectly tracked points.

The images were acquired on the same magnet using the same basic imaging protocol as in the canine studies described hereinabove. SPAMM tags were generated at end-diastole to achieve saturation planes orthogonal to the image plane separated by 7 mm. Two sets of images with vertical and horizontal tags were acquired in separate breath-holds. Four slices were acquired, but only the midwall-basal slice is used in this example. Scanner settings were as follows: field of view 36-cm, tag separation 7-mm, 8-mm slice thickness, TR=6.5-ms, E=2.3-ms, 15° tip angle, 256× 160 image matrix, 5 phase-encoded views per movie frame.

Figure 16A:
FIG. 16(a) illustrates a normal human heart undergoing dobutamine induced stress including the short-axis images and tracked circles from the first or top-left representation to the last bottom-right representation without HARP refinement.
Figure 16B:
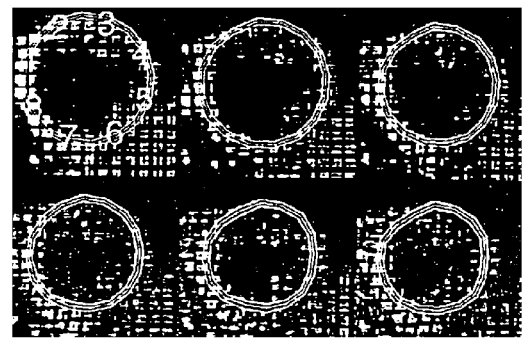
FIG. 16(b) is similar to FIG. 16(a), but illustrates the result after application of HARP refinement.

FIG. 16(a) shows the resulting horizontal and vertical tagged images multiplied together and cropped to a region of interest around the LV. The contours appearing in these images were generated by manually placing epicardial and endocardial circles in the first image and tracking them forward in time using HARP tracking. Because of large motion between the first and second time frames, several points on the anterior free-wall were mistracked in the second frame. This error was not corrected in the remaining frames because the basic HARP tracking approach uses the previous tracked point as an initialization in the current frame. The result of applying HARP refinement using three manually identified anchors (one on each circle) within the septum is shown in FIG. 16(b). By visual inspection, one can see that the refined result has placed the tracked points where one would expect them in each time frame. Tag jumping has been eliminated.

Figure 16C:
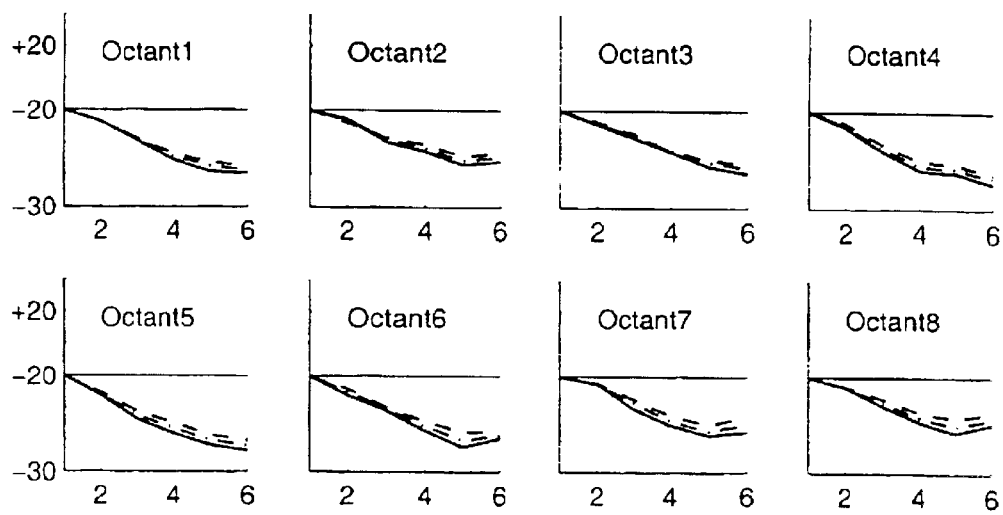
FIG. 16(c) illustrates the temporal evolution of circumferential strain calculated using the refined points.

Using the refined tracking result, the temporal evolution of circumferential strain in each quadrant was calculated. The result is shown in FIG. 16(c). These plots show fairly uniform shortening throughout the LV with the strongest persistent shortening in the free wall. These results also demonstrate the greatest shortening occurring in the endocardium, as is usual in normal muscle.

In order to make a quantitative comparison with accepted prior art methods, two preliminary analyses of the accuracy of HARP tracking in comparison to matched filtering, which is the basis of an accepted technique known as FindTags were conducted (T. S. Denney, "*Identification of myocardial tags in tagged MR images without prior knowledge of myocardial contours,*" In J. Duncan and G. Gindi, editors, Proc. Inf. Proc. Med. Imag., pages 327–340, 1997). The accuracy of FindTags has been shown both in theory and phantom validation to be in the range of 0.1 to 0.2 pixels depending on the contrast to noise ratio (CNR) of the image (Moore et al., "*Tagged MR imaging in a deforming phantom: photographic validation,*" Radiology, 190:765–769, 1994). The results show that the accuracy of HARP is the same as or better than matched filtering approaches.

Figure 17A:
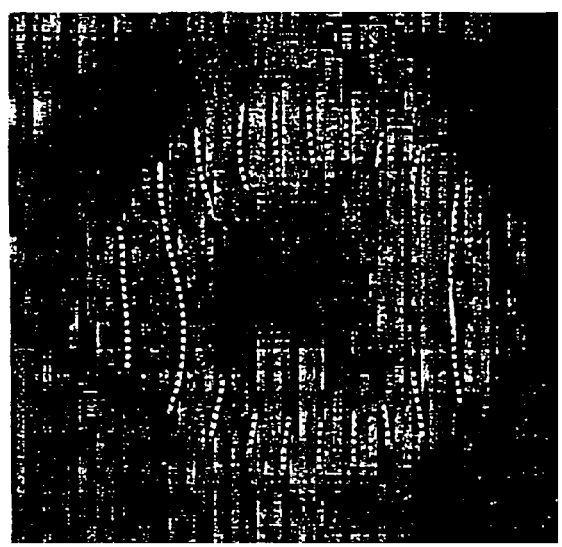
FIG. 17(a) illustrates HARP accuracy in comparison to FindTags employing normal human data with a tagged image with tag points from FindTags (block dots) overlaying HARP $\pi$ isocontours (white curves).

Next, attention was directed to finding tag lines using data from a normal human subject. FindTags was used to estimate both the contours (endocardium and epicardium) and the tag lines in 27 images from a vertical tagged, short axis data set comprising 9-image sequences from three longitudinal positions within the LV. HARP images were generated from these nine images using the first harmonic and a bandpass filter similar to the one shown in FIG. 8(b). Theory predicts that tag bottoms should be located at a phase angle of $\pi$ radians, and therefore $\pi$ isocontours of HARP images should be very close to the tag points identified by FindTags. FIG. 17(a) superposes tag points from FindTags onto these HARP isocontours in a mid-ventricular image taken at the seventh time frame, where significant tag fading has occurred.

There were only minor differences between HARP isocontours and tag contours estimated using FindTags. HARP appears to yield a very slightly smoother result, the main difference being a slight fluctuation around the HARP result on the free wall (3 o'clock). It is difficult to conclude which is more visually satisfying. The average HARP angle calculated using the entire collection of FindTags tag points is very close to $\pi$ (to three significant digits), verifying the theoretical prediction that tag bottoms should have a HARP angle of $\pi$. Local phase unwrapping was employed in order to compute this average angle as $\pi$ corresponds exactly to the location of a wrapping artifact in HARP images.

Figure 17B:
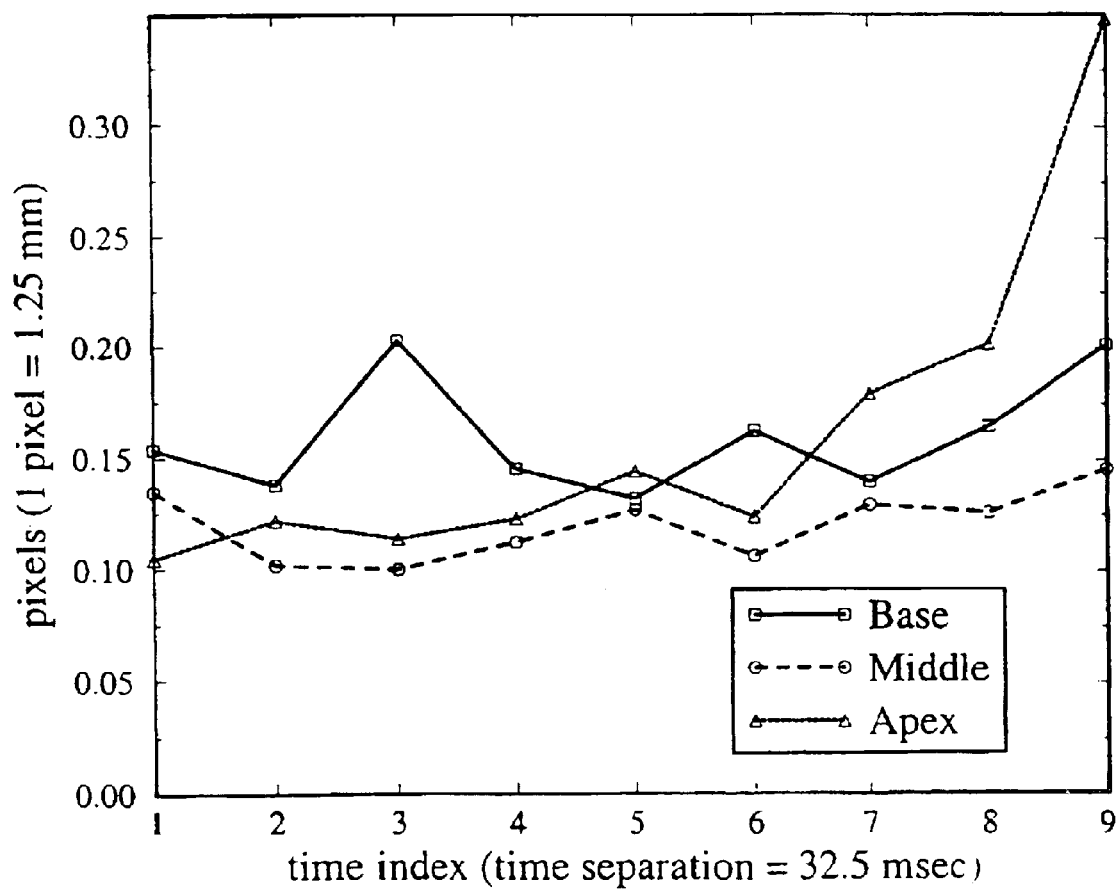
FIG. 17(b) shows the average distance between the Find-Tags tag points and the HARP isocontour.

To arrive at a quantitative measure of accuracy, the distance between each tag point and the nearest HARP $\pi$ radian isocontour in the same image was calculated. The root-mean-square (rms) distance over all times and spatial positions was approximately 0.15 pixels. Plots of the average distances as a function of time for the basal, midventricle, and apical short-axis images are shown in FIG. 17(b). If FindTags represented the truth, then it could be concluded that HARP has roughly 0.15–0.25 pixel error. As these average distances are on the same order as the intrinsic error in FindTags, it is correct to draw this conclusion. In fact, HARP may have significantly less error, in which case these distances simply represent the intrinsic error of FindTags. It is also possible, however, that HARP may have this error in addition to that of FindTags, in which case HARP would have approximately 0.3 pixel average error. It was concluded that HARP tracking error are approximately the same as those of FindTags.

HARP tracking uses two HARP images simultaneously, and is more like finding tag line crossings than tag lines themselves. As a result, in this experiment, HARP tracking was compared with tag line crossing estimation using FindTags. Using the paced canine heart data described herein, FindTags were used to compute the positions of all tag lines, both vertical and horizontal, in the 20-image basal short-axis image sequence. Using the endocardial and epicardial contours, also estimated using FindTags, the tag line intersections falling within the myocardium were computed. HARP tracking was then run on each of these points seeking the target vector $a=[\pi\pi]^T$ radius, including the first timeframe.

Figure 18:
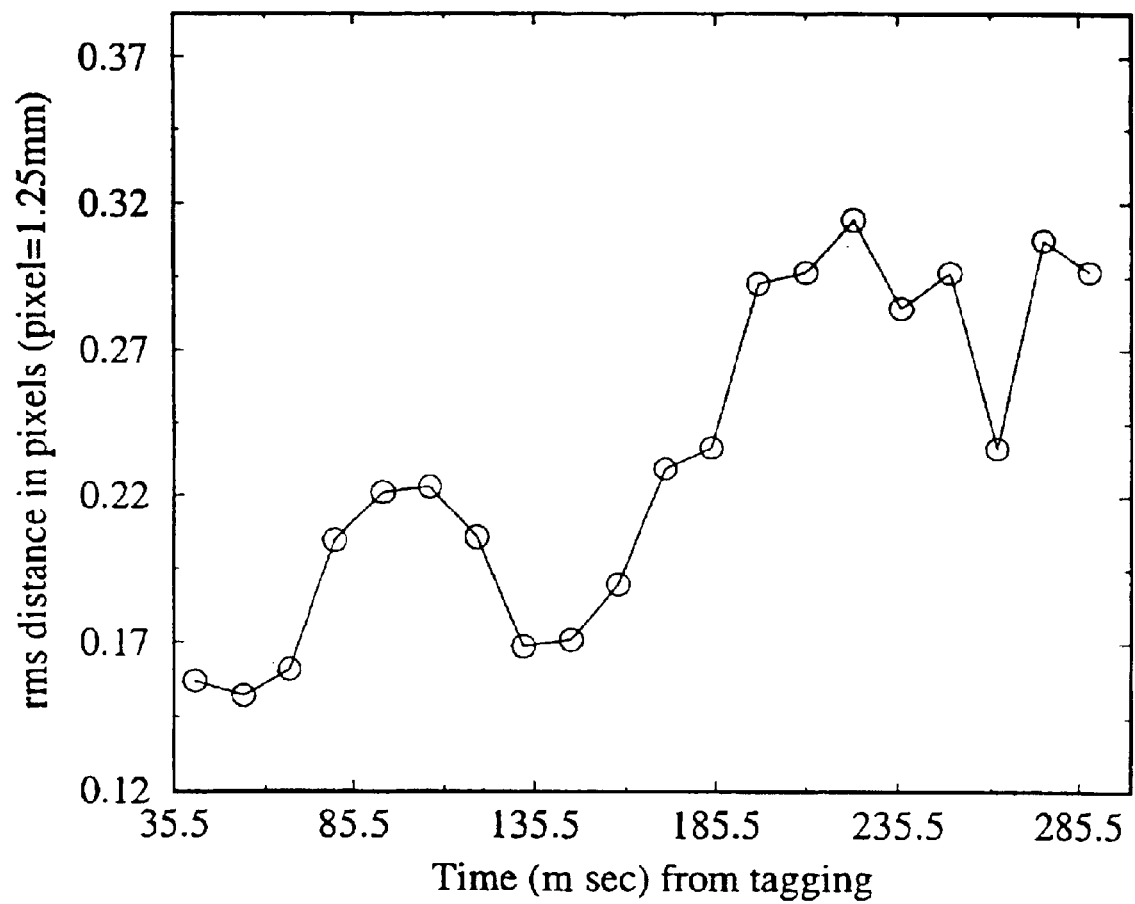
FIG. 18 illustrates a plot of the average difference in tag crossing estimation between FindTags and HARP.

The root-mean-square distance between the FindTags intersections and the HARP tracked points is shown as a function of time in FIG. 18. These errors are somewhat larger than the previous experiment. This can be mostly accounted for by noting that when seeking two lines instead of just one, the error should go up by approximately $\sqrt{2}$. Other minor differences can be accounted for by the different experimental setups and imaging protocols. The general trend of increasing distance over time is also to be expected because the signal-to-noise ratio drops as the tags fade.

One interesting feature in the plot in FIG. 18 is the "hump" occurring in time frames 4–7. One possible explanation lies in the placement of the bandpass filter used in HARP. As normal cardiac motion during systole is a contraction, the local frequency of the fundamental tag harmonic generally increases. Also, as tags fade, the DC spectral peak increases in energy causing interference with the spectrum around the first harmonic. Our usual practice, therefore, is to place the bandpass filter at slightly higher frequencies, to simultaneously capture the higher frequency spectrum associated with contraction and to avoid interference from the DC spectral peak. However, frames 4–7 are precisely where the pre-stretching phenomenon in this paced data is most prominent, as can be seen in FIGS. 11 and 15 and this causes the local frequency of tags to decrease rather than increase. This part of the spectrum may be getting cut off in the filter, leading to slightly higher differences and probably increased errors.

In the foregoing experiments, all the computations, including the HARP tracking method and the Lagrangian strain computations were done on a 400 MHz Intel Pentium II processor using MATLAB (The Mathworks, Natick, Mass.). Despite the fact that we have not optimized our MATLAB code (to eliminate loops, for example) HARP processing is very fast in comparison to other methods of which we are aware. For the paced canine heart, computation of 20 vertical and 20 horizontal HARP images took about 30 seconds. Positioning endocardial and epicardial circles within the LV myocardium takes about 20 seconds of human interaction. Tracking the 48 points defined by this process through all 20 time frames took only about 5 seconds, and the computation of the Lagrangian strain also took only about 5 seconds. The overall time from images to strain takes only about 2 minutes, which includes time to click on buttons and arrange images. There is potential for significant streamlining of certain steps, as well.

The organization of image data and the definition of the bandpass filters also adds time to the overall processing time of HARP analysis. On standard scans these times are negligible, and the image sequences can be constructed automatically and preset bandpass filters can be used. On special scans or new experimental protocols, some additional time may be spend in preparing the data for HARP processing. A user skilled in the art can generally perform these additional steps in less than 30 minutes, and a convenient user interface will reduce this time even further. HARP will be useful for clinical use with further minor validation and optimization.

We previously suggested a method for computing optical flow, a dense incremental velocity field, using HARP images (Osman et al., "*Imaging heart motion using harmonic phase MRI,*" October 1998). This HARP optical flow method used the idea of the HARP angle as a material property and the notion of apparent motion, but it did not iteratively seek the point sharing two HARP values. Instead, it used the ideas of multiple constraint optical flow to directly and rapidly compute an approximate location of each pixel in the next image frame using a simple 2-by-2 matrix inverse at each pixel. If applied to every pixel in an image and tracked only to the next time frame, HARP tracking would essentially give the same result only with greater accuracy. It would also require significantly more time, perhaps 4–5 times longer. The HARP optical flow method may be useful in initializing HARP tracking or in yielding very rapid and dense motion fields for visualizing motion or calculating other motion quantifies on a dense mesh.

It will be appreciated that in the methods of the present invention, the material property of HARP angle was exploited to develop a two-dimensional HARP tracking method that is fast, accurate, and robust. Points were tracked in a coordinate system that was used to directly compute both circumferential and radial Lagrangian strain in the left ventricle. Experiments on a paced canine heart demonstrated the ability for HARP to track abnormal motion and to compute strains that are consistent with previous reported analysis. A refinement technique for the correction of incorrectly tracked points was developed and demonstrated on a normal human heart undergoing dobutamine stress. Finally, a preliminary error analysis was conducted showing that HARP tracking compares very favorably with FindTags, a standard template matching method. HARP tracking and Lagrangian strain analysis was shown to be computationally very fast, amenable to clinical use after suitable further validation.

While for purposes of simplicity of disclosure, specific reference has been made to medical applications of the methods of the invention, the method is not so limited and may be employed in a wide variety of industrial and other uses.

Whereas, particular embodiments of the invention have been described herein for purposes of illustration, it will be evident to those skilled in the art that numerous variations of the details may be made without departing from the invention as defined in the appended claims.

We claim:

1. A method of measuring motion of an object by magnetic resonance imaging comprising applying a pulse sequence to spatially modulate a region of interest of said object;

acquiring at least one first spectral peak from the Fourier domain of said spatially modulated object;

computing the inverse Fourier transform information of said acquired first spectral peaks;

computing a first harmonic phase image from each said spectral peak;

repeating said process with respect to a different time to create a second harmonic phase image from each second spectral peak; and determining strain from said first and second harmonic phase images.

2. The method of claim 1 wherein the object includes a heart.

3. The method of claim 2 wherein the step of determining strain comprises determining circumferential Lagrangian strain.

4. The method of claim 3 wherein determining strain includes determining at least one of endocardial, epicardial and midwall strain.

5. The method of claim 3 further including employing positive strain values as an indication of circumferential stretching and negative strain values as an indication of circumferential contraction.

6. The method of claim 2 wherein the determining strain includes determining radial Lagrangian strain.

7. The method of claim 6 determining at least one of endocardial and epicardial radial strain.

8. The method of claim 6 further including employing positive strain values as an indication of radial thickening and negative strain values as an indication of radial thinning.

9. The method of claim 2 wherein determining strain includes determining strain in the myocardium.

10. The method of claim 2 further including employing a refinement procedure in tracking said motion.

11. The method of claim 10 wherein employing a refinement procedure includes employing an anchor point which has relatively small motion as a tracking reference.

12. The method of claim 11 wherein employing a refinement procedure includes employing a sequence of points each of which is separated from the next adjacent point by less than one pixel.

13. The method of claim 12 wherein employing a refinement procedure includes effecting said refinement procedure in a generally radial path.

14. The method of claim 1 wherein the first harmonic phase image and the second harmonic phase image comprise two-dimensional images.

15. The method of claim 1 wherein the object includes a moving human heart.

16. The method of claim 15 wherein determining strain includes measuring motion within the left ventricular of said heart.

17. The method of claim 15 wherein the step of applying a pulse is initiated generally at end-diastole.

18. The method of claim 1 wherein applying a pulse sequence includes employing SPAMM pulse sequence.

19. The method of claim 1 wherein the first harmonic phase image and the second harmonic phase image include three-dimensional images.

20. The method of claim 1 wherein determining strain includes determining the spacing between a point at different times.

21. The method of claim 20 wherein determining the spacing between a point at different times includes determining said strain by tracking the apparent motion of said points in an image plane and determining Lagrangian strain from said tracked points.

22. The method of claim 21 further including tracking said apparent motion through a CINE sequence of tagged magnetic resonance images.

23. The method of claim 1 wherein determining strain includes measuring an increase in distance between a point at two different times.

24. The method of claim 1 wherein determining strain includes measuring a decrease in distance between a point at two different times.

25. The method of claim 1 wherein the first harmonic phase image and the second harmonic phase image include both horizontal and vertical tagged images.

26. The method of claim 1 wherein computing a first harmonic phase image includes employing a bandpass filter in computing the first harmonic phase image.

27. The method of claim 1 wherein determining strain includes employing said first and second harmonic phase images substantially simultaneous.

* * * * *